(12) United States Patent
Zamadar

(10) Patent No.: US 11,850,233 B2
(45) Date of Patent: Dec. 26, 2023

(54) REDUCED ADAPTIVE MICROBIAL RESISTANCE TREATMENT FOR FLESH EATING DISEASE (NECROTIZING FASCIITIS)

(71) Applicant: Matibur Rahaman Zamadar, Nacogdoches, TX (US)

(72) Inventor: Matibur Rahaman Zamadar, Nacogdoches, TX (US)

( * ) Notice: Subject to any disclaimer, the term of this patent is extended or adjusted under 35 U.S.C. 154(b) by 741 days.

(21) Appl. No.: 16/666,323

(22) Filed: Oct. 28, 2019

(65) Prior Publication Data

US 2021/0121441 A1    Apr. 29, 2021

(51) Int. Cl.

| | |
|---|---|
| A61K 31/409 | (2006.01) |
| A61K 33/30 | (2006.01) |
| A61K 33/32 | (2006.01) |
| A61K 33/26 | (2006.01) |
| A61K 8/49 | (2006.01) |
| A61K 8/19 | (2006.01) |
| A61K 41/00 | (2020.01) |
| A01N 43/40 | (2006.01) |
| A61Q 17/00 | (2006.01) |

(52) U.S. Cl.
CPC ............ *A61K 31/409* (2013.01); *A01N 43/40* (2013.01); *A61K 8/19* (2013.01); *A61K 8/4926* (2013.01); *A61K 33/26* (2013.01); *A61K 33/30* (2013.01); *A61K 33/32* (2013.01); *A61K 41/0071* (2013.01); *A61Q 17/005* (2013.01)

(58) Field of Classification Search
CPC ...... A61K 31/409; A61K 8/19; A61K 8/4926; A61K 33/26; A61K 33/30; A61K 33/32; A61K 41/0071; A01N 43/40; A61Q 17/005
See application file for complete search history.

(56) References Cited

U.S. PATENT DOCUMENTS

| | | | |
|---|---|---|---|
| 4,946,688 | A | 8/1990 | Fahim |
| 5,071,658 | A | 12/1991 | Fahim |
| 6,087,493 | A | 7/2000 | Wheelhouse |
| 7,026,347 | B2 | 4/2006 | Frydman et al. |
| 7,163,919 | B2 | 1/2007 | Bae |
| 8,592,404 | B2 | 11/2013 | Periera |
| 8,796,252 | B2 | 8/2014 | Rioux et al. |
| 8,952,357 | B2 | 2/2015 | Yamada et al. |
| 9,517,277 | B2 | 12/2016 | Dhar |
| 9,968,537 | B2 | 5/2018 | Sharma |
| 10,124,064 | B2 | 11/2018 | Herr |
| 10,286,004 | B2 | 5/2019 | Kim et al. |
| 10,314,312 | B2 | 6/2019 | Sharma |
| 10,342,750 | B2 | 7/2019 | Prencipe et al. |
| 10,407,435 | B2 | 9/2019 | Shuttleworth et al. |

FOREIGN PATENT DOCUMENTS

| | | |
|---|---|---|
| CN | 201910134653.1 A | 2/2019 |
| KR | 1020010029784 A | 5/2001 |
| WO | 03018006 A1 | 3/2003 |

OTHER PUBLICATIONS

N. Karakostas et al. Journal of Photochemistry and Photobiology A: Chemistry 213 (2010) 52-60 (Year: 2010).*

Hanakova et al., Study of photodynamic Effects on NIH 3t3 Cell Line and Bacteria, Biomed Pap Med Fac Univ Palakcy Olomouc Czech Repub, 2014, 201-207, 158.

Grinhole et al., Fine-tuning rec A expression in *Stahylococcus aureus* for antimicrobial photoinactivation: importance photo-induced DNA damage in the photoinactivation mechanism, Appl Microbiol Biotechnol, 2015, 9161-9176, 99.

Awad et al., Important cellular targets for antimicrobial photodynamic therapy, Appl Microbial Biotechnol, 2016, 7679-7688, 100.

Thomas et al., Amphiphilic cationic Zn-porphyrins with high photodynamic antimicrobial activity, Future Microbiol., 2015, 709-724, 10(5).

Zamani et al., Photo-modulation of zinc phthalocyanine-treated breased cancer cell line ZR-75-1 inhibitied the normal tumor activity in vitro, Lasers in Medical Science, 2018.

Parida et al., Tunable photophysical processes of phorphyrin macrocycles on the surface of ZnO nanoparticles, J. Phys. Chem. C, 2015, 2614-2621, 119, 1969-1978.

Hanakova et al., The application of antimicrobial photodynamic therapy on *S. aureus* and *E. coli* using porphyrin photosensitizers bound to cyclodextrin, Microbiological Research 169, (2014) 163-170.

Skwor et al, Photodynamic inactivation of methicillin-resistant *Staphylococcus aureus* and *Escherichia coli*: A metalloporphyrin comparison, Journal of Photochemistry & Photobiology, 2016, 51-57.

Al-Mutairi et al., Sublethal Photodynamic Treatment Does Not Lead to Development of Resistance, Photodynamic Therapy and Antimicrobial Resistance, 2018, 1-9.

(Continued)

*Primary Examiner* — Jeffrey S Lundgren
*Assistant Examiner* — William Y Lee
(74) *Attorney, Agent, or Firm* — William R. Childs; Childs Patent Law PLLC

(57) ABSTRACT

Next generation therapeutics for treatment of microorganisms (especially bacterium, fungus or certain virus) and cancer and for fluorescence diagnosis are provided. Association complex(es) effective as bactericides are formed in situ by loose interactions of molecular entities. Adjustable variable associations reduce chance bacteria develops adaptive resistance versus a single bactericide structure or method. Multifunctional variations simultaneously or sequentially attack target cells and adjust level of reactive oxygen species produced such as singlet oxygen. Claimed systems are effective bactericides in aerobic and anaerobic conditions and in absence of or presence of visible light. In presence of visible light in aerobic conditions, such are cancer treatments. Preferred are water soluble, nontoxic association complex(es). Variations can be formed by varying porphyrins and interacted metal ions, for illustration, tetrakis Ar substituted porphyrin without bound metal at core but combined with divalent metals of spatial and/or charge density characteristics similar to Zn(II) such as Co(II), Fe(II), and Mn(II).

15 Claims, 7 Drawing Sheets

(56) References Cited

OTHER PUBLICATIONS

Faiz et al., Efficacy of Zinc as an Antibacterial Agent Against Enteric Bacterial Pathogens, J Ayub Med Coll Abbottabad, 2011, 18-21.

Khurana et al., Supramolecular Nanorods of (N-Methylpyridyl) Porphyrin With Captisol: Effective Photosensitizer for Antibacterial and Anti-tumor Activites, Frontiers in Chemistry, 2019, 1-11.

Chen et al., Formulation and Evaluation of Antibacterial Creams and Gels Containing Metal Ions for Topical Application, Journal of Pharmaceutics, 2016, 1-10.

Zhou et al. Antibacterial Polypeptide-Grafted Chitosan-Based Nanocapsules As an "Armed" Carrier of Anticancer and Antiepileptic Drugs, ACS Macro Letters, 2013, 1021-1025.

Mesquita et al. Revisiting Current Photoactive Materials for Antimicrobial Photodynamic Therapy, Molecules, 2018, 1-47.

Chaves et al. Free-Base and Metal Complexes of 5, 10, 15,20-Tetrakis(N-Methyl Pyridinium L)Porphyrin: Catalytic and Therapeutic Properties, Phtalocyanines and Some Current Applications, 2017, 1-28.

He et al. Tetracyclines function as dual-action light-activated antibiotics, PLOS ONE, 2018, 1-15.

Singh et al. Dual functionality nanobioconjugates targeting intracellular bacteria in cancer cells with enhanced antimicrobial activity, Scientific Report, 2017, 1-10.

Chen, et al. Efficient Bacterial Inactivation by Transition Metal Catalyzed Auto-Oxidation of Sulfite, Environmental Science & Technology, 2017, 12663-12671.

Benov, et al. Isomeric N-alkylpyridylporphyrins and their Zn(II) complexes inactive as SOD mimics but powerful photosensitizers, Archive of Biochemistry and Biophysics, 2002, 159-165.

Plum, et al. The Essential Toxin: Impact of Zinc on Human Health, Int. J. Environ. Res. Public Health, 2010, 7, 1342-1365.

Benov, et al. Protein damage by photo-activated Zn(II) N-alkylpyridylporphyrins, 2012, 117-128.

Ezzeddine et al. Effect of Molecular Characteristics on Cellular Uptake, Subcellular Localization, and Phototoxicity of Zn(II) N-alkylpyridylporphyrins, J. Biological Chemistry, 2013, 36579-36588.

Al-Mutairi, et al., Photosensitizing action of isomeric zinc N-methylpyridylporphyrins in human carcinoma cells, Free Radical Research, 2006, 477-483.

\* cited by examiner

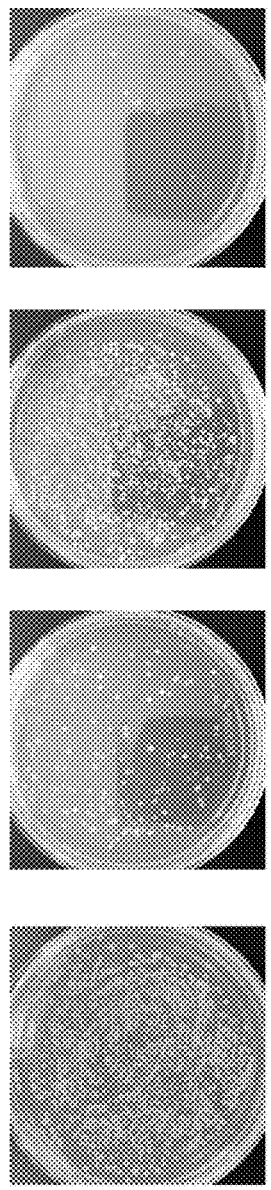
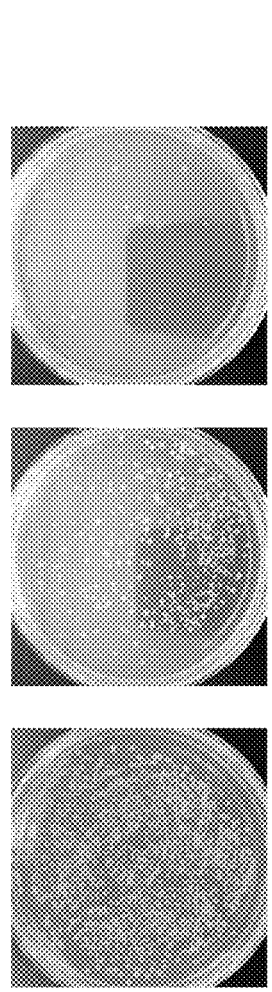
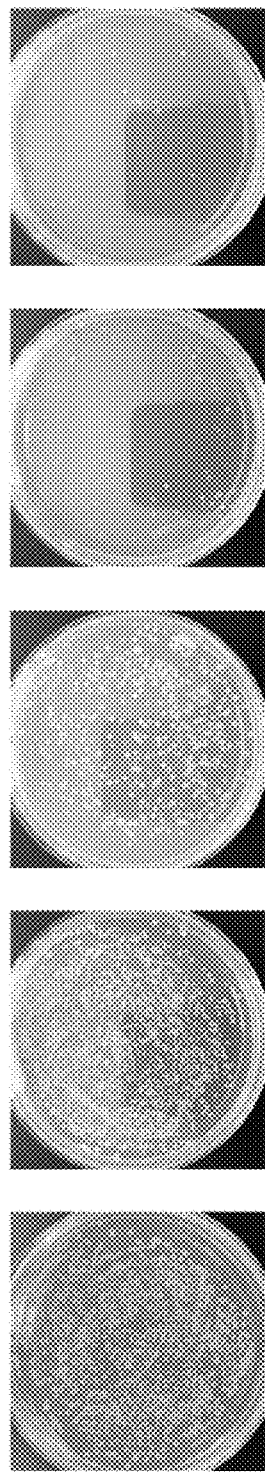
FIG. 1A  FIG. 1B  FIG. 1C  FIG. 1D
FIG. 2A  FIG. 2B  FIG. 2C
FIG. 3A  FIG. 3B  FIG. 3C  FIG. 3D  FIG. 3E Zn(II)TMPyP One embodiment of (TMPyP+Zn(II))

TMPyP

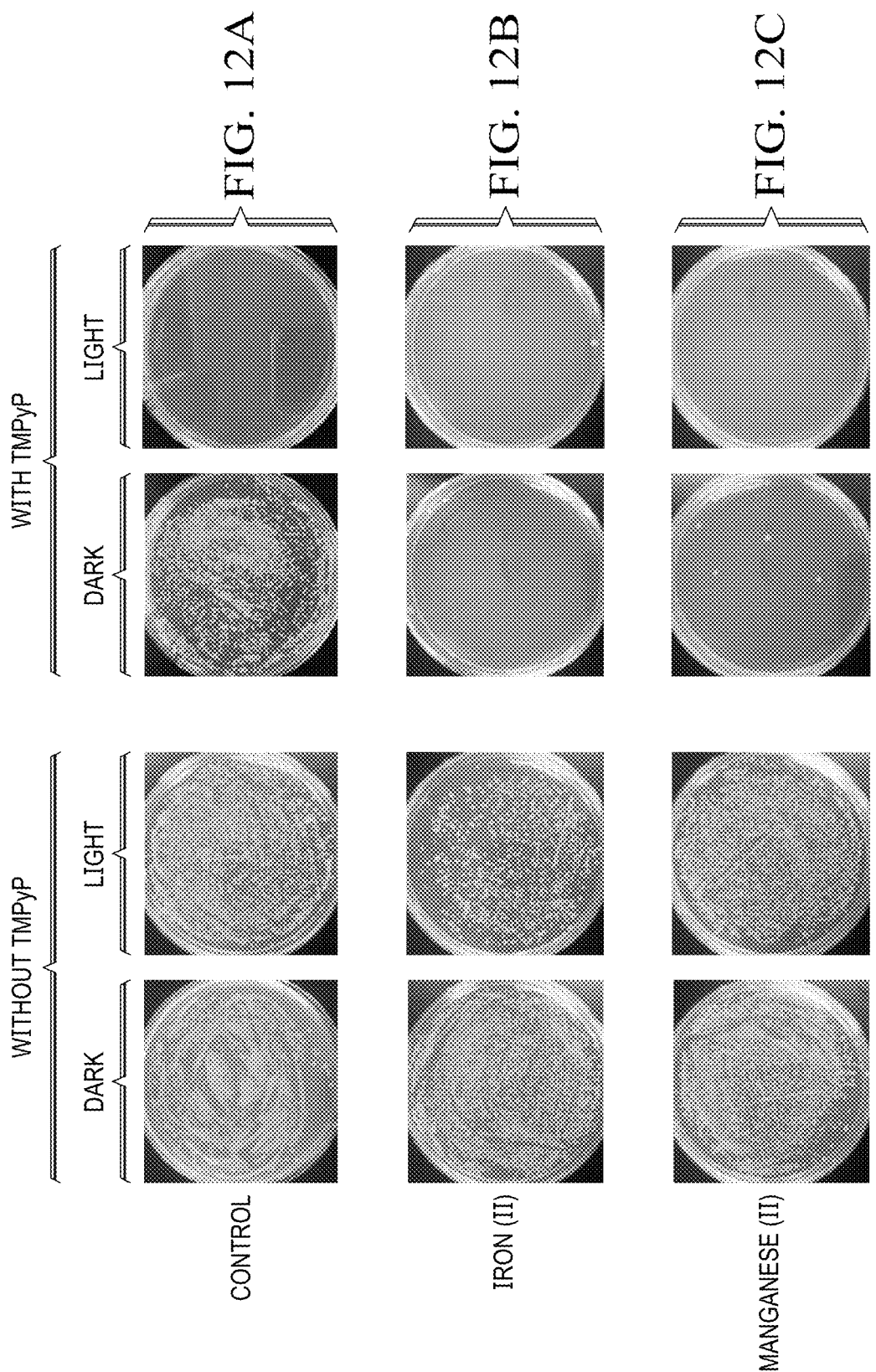

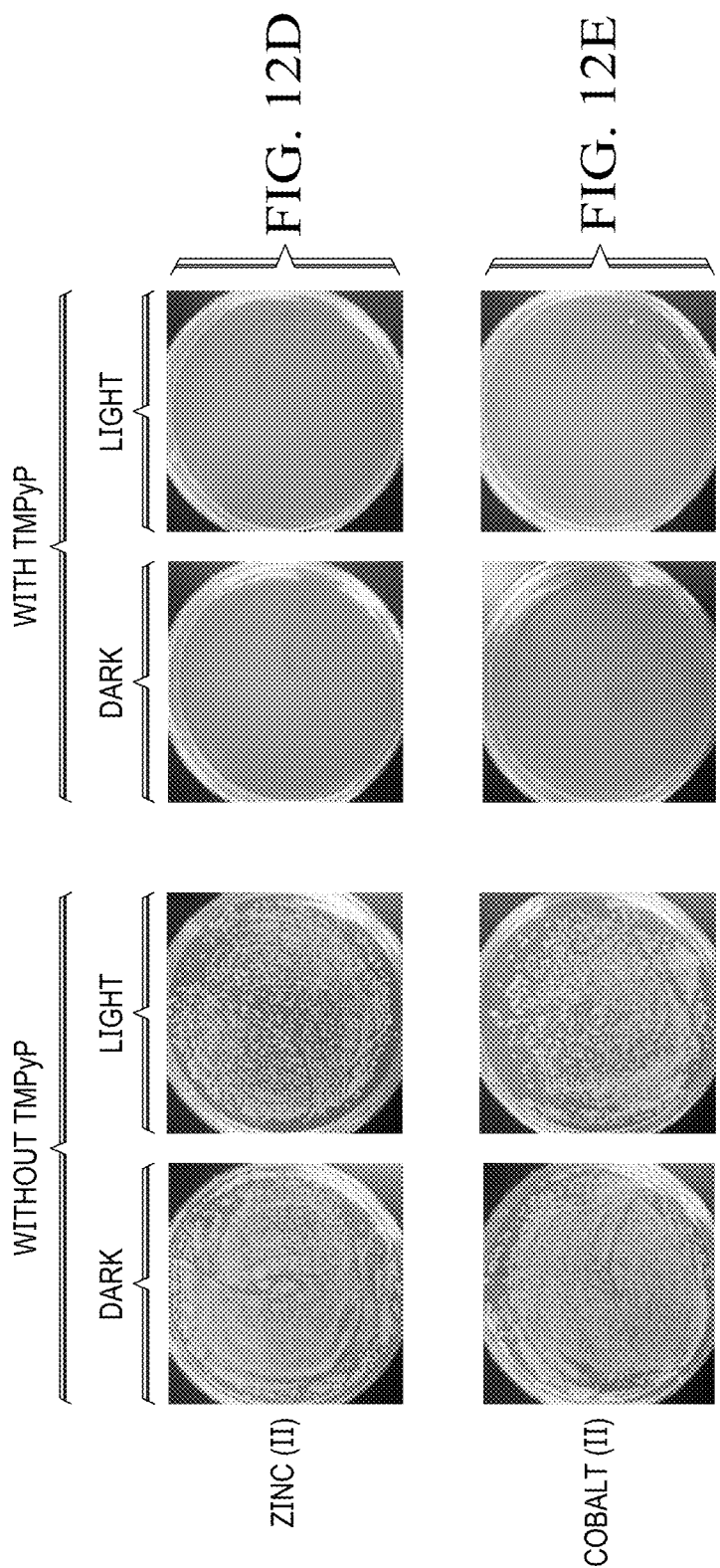

REDUCED ADAPTIVE MICROBIAL RESISTANCE TREATMENT FOR FLESH EATING DISEASE (NECROTIZING FASCIITIS)

GOVERNMENT RIGHTS IN INVENTION

This invention was made with support from Research and Creative Activity grant by Texas' Stephen F. Austin State University Research Enhancement Program (RCA) and Texas Research Grant Funding pursuant to The Welch Foundation (AN-0008 Departmental Grant). While neither above mentioned support sources is directly Federally Sponsored Research or Development, the government may have indirect rights in this invention for research, educational, and clinical purposes.

BACKGROUND OF THE INVENTION

1. Field of the Invention

This invention relates to antimicrobial compositions and methods that avoid or reduce antimicrobial resistance. For example, antibiotic resistance occurs when medication loses its ability to kill bacteria.

This invention relates to bactericides having adjustable or random association of components to avoid single fixed structure against which bacteria adapt to become resistant.

This invention also relates to antibacterial agents effective at relatively low single dose or reduced repeat doses.

This invention further relates to antibacterial agents for treatment of skin issues, especially flesh eating bacteria, wherein an antibacterial agent effective in light conditions is required. Many typical antibiotics work in dark conditions but are not effective in light conditions.

In one aspect, this invention relates to porphyrin containing compositions for treating bacteria in dark conditions, whereas most porphyrin based antibiotics are ineffective in dark conditions. In one variation of this invention, compositions are provided which treat bacteria in absence of visible light, or in presence of light, in aerobic and/or anaerobic environments.

This invention also relates to multimodal treatment compositions and methods for treating bacteria and cancer, simultaneously or in sequence. In one aspect, this invention also relates to treatment compositions and methods effective against cancer cells in the presence visible light in aerobic environments and also effective to treat bacterial infection complications of cancer treatment. As part of surgical removal of portions of cancerous cells, damages to remaining tissue and associated bacteria growth often result, with remaining tissue in need of antibacterial and as well as anticancer treatment. Many cancer drugs are unable to treat bacterial infections in cancer patients.

This invention also relates to treatment compositions which possess antibacterial and photodynamic therapy (PDT) properties and are effective against cancers in aerobic conditions in presence of light. Provided are variations of treatment through antimicrobial photodynamic inactivation (aPDI) and enhanced PDT features.

Furthermore, the present invention relates to compositions with capability to be administered for sequential or simultaneous therapies, for example cancer treatment followed by bacteria treatment or treatment for bacterial infections followed by cancer treatment via PDT, as well as simultaneous treatments.

A specific aspect of this invention relates to compositions comprising one or more free base tetrakis Ar substituted porphyrin core without metal or halide substitution but having ortho- meta-, or para-hydroxyphenyl, N-alkylphenyl, carboxylatephenyl, sulfonatephenyl, and alkyl pyridyl substituents in meso positions and further comprising one or more divalent hydrated metal ions having similar spatial characteristics, and/or similar charge density, to hydrated $Zn(II)$ ions. More particularly, this invention relates to combinations with dual functionality of results of combination, such as the specific embodiment of combination of (i) cationic meso-tetra(N-methyl-4-pyridyl)porphyrin tetrachloride (TMPyP) with (ii) $Zn(II)$ ions in aqueous solution and the association complex(es) formed and other resultant effects of such combination.

It is important that I have discovered treatment compositions that can easily be prepared from commercially available chemicals, and without special synthesis equipment, skills or training required, allowing potential for them to be readily available at lower cost in developing and developed countries. Variations of my claimed treatment compositions are water soluble and nontoxic. As demonstrated by the Examples, short preparation and application times for compositions of this invention enable rapid, effective field treatments, and may include certain diagnosis, in locations at which any kind of treatments or diagnosis were heretofore prohibited.

2. Description of the Related Art

Pathogenic bacteria often develop resistance against conventional antibacterial agents, which lose efficacy over time. By developing familiarity with structure of bactericide (adaptive bacterial resistance), many bacteria adapt and become resistant to specific antibacterial structures. As bacterial resistance increases to specific antibacterial structure or composition, dosages are increased until highest doses become ineffective against the then most resistant bacteria. Thus, dosage abuses of antibiotics often lead to the emergence of more resistant pathogens.

Since about 1970s, no major developments for new classes of antibiotics have been reported except synthetic antibacterial agents (oxadiazoles).

Studies project that by 2050 antibacterial resistance will kill 300 million people worldwide, and total world economic loss will be around $100 trillion if antibacterial resistance is not addressed. Also, conventional antibiotics are costly, not easily synthesized or readily available to poorer developing or certain developed countries.

Patients receiving extended cancer treatment are at high risk of developing bacterial infections and bacterial resistance due to prolonged neutropenia, lymphocyte dysfunction, mucositis, and use of invasive devices. Chemotherapy drugs usually cannot target bacteria in specific manner and are therefore unable to eliminate live bacteria from the tumor site.

Physicians often administer a high dose of antibiotics to cancer patients undergoing cancer treatment. For example, physicians may administer higher doses of antibiotics to immunologically impaired cancer patients.

Certain excessive doses of traditional antibiotics may cause adverse side effects for patients after tumor surgery. In such therapy, some conventional antibacterial agents are reported to lack target selectivity and have poor water solubility and poor bio-distribution, and some are blamed for mutagenic and carcinogenic side effects.

Antimicrobial photodynamic inactivation (aPDI) is widely recognized, clinically proven method against a number of antibiotic-resistant microorganisms such as Gram-positive and Gram-negative bacteria and certain fungi. Effective aPDI methods usually employ nontoxic photosensitizers (PSs), light, and oxygen for the treatment. Photosensitizers produce reactive oxygen species (ROS), such as singlet oxygen ($^1O_2$) or hydroxyl radicals (OH) upon reacting with ambient oxygen ($O_2$) in the presence of visible light. Improved medically useful PSs are needed because reactive oxygen species (ROS) can cause severe oxidative damages to kill microbial cells and that singlet oxygen ($^1O_2$) is the primary microbial cell damaging factor for most PSs.

Zinc metal is a trace metal that is a necessary nutrient to the human body. Forms of zinc are reported to have a number of health benefits including developing stronger immune system, reducing diarrhea symptoms, enhancing learning and memory, addressing common cold, providing wound healing, decreasing risk of age-related chronic disease, preventing age-related macular degeneration and others.

Zinc bound compounds such as zinc oxide, zinc sulfate, zinc sulfate-copper sulfate, zinc pyrithione, zinc-phthalocyanine, and zinc salt of pyridine carboxylic acid have been used for *E. coli* inactivation.

However, said zinc-containing compounds do not exhibit multifunctional properties, being incapable of attacking target cells by multiple ways. They are unable to address bacterial resistance issue since such are often used at high concentrations for bacteria inactivation leading to situations where bacteria become more resistant over time thereby diminishing effectiveness of applied antibacterial.

Bound metallized porphyrins (wherein metal is bound at core, for illustration stable ZnPorphyrins) and their chemical properties are thus many decades old chemistry. Such bound metallized porphyrins have been used in many applications such as solar energy, sensing, antibacterial, anticancer and many other applications.

Zinc bound compounds such as ZnTMPyP (commercially available Zn(II) covalently bound meso-tetrakis(N-methyl-4-pyridyl) porphyrin) and ZnTPPS$_4$ (commercially available Zinc-5,10,15,20-tetrakis(4-sulphonatophenyl) porphyrin) have been used for bacteria inactivation in light, aerobic conditions, but not in dark conditions.

Reported also to inhibit *E. coli* growth in light (but not in dark) aerobic conditions are Zn bound-to-porphyrin core compounds such as (a) Zn(II) meso-tetrakis(N-alkylpyridinium-2-yl)porphyrins as reported by Award, M. et al, (2016) "Important cellular targets for antimicrobial photodynamic therapy" *Appl Microbiol Biotechnol* 100, 7679-7688, (b) Zn(II) meso-tetrakis(Nhexylpyridinium-2-yl)porphyrins as reported by Al-Mutairi, R. et al (2018) "Sublethal photodynamic treatment does not lead to development of resistance" *Frontiers in Microbiology* 9, 1-9, and (c) Zinc-5,10,15,20-tetrakis(4-sulphonatophenyl) porphyrins (ZnTPPS$_4$) as reported by Hanakova, A. et al (2014) "Study of photodynamic effects on NIH 3T3 cell line and bacteria" *Biomed Pap Med Fac Univ Palacky Olomouc Czech Repub* 158, 201-207.

Also, free base meso-tetra(N-methyl-4-pyridyl) porphyrin tetrachloride (alone without metal) inhibits *E. coli* growth in light, aerobic conditions as reported by Khurana, R. et al (2019) "Supramolecular nanorods of (N-Methylpyridyl) porphyrin with captisol: effective photosensitizer for antibacterial and anti-tumor activities" Frontiers in Chemistry 7, 1-11.

However, rigid structures of conventional bound metal-porphyrin compounds are not an active form complex for therapeutic application in dark conditions, even if in solution.

For example, said zincporphyrins and other bound zinc containing compounds are unable to slow/stop the growth of bacteria in absence of visible light and in hypoxic (lack of oxygen, anaerobic) environments. Some are not fully effective even at high concentrations, tending to demand high dosage levels. Also, most such bound zinc containing compounds are costly to synthesize and cannot be readily prepared remotely without synthesis equipment or without extensive synthesis training.

Bound metal metallated porphyrins exhibit desirable properties that the individual components do not exhibit (e.g. exhibit properties not shown by the metal alone or the porphyrin alone). For example, individual components (e.g. of such bound metallized porphyrin) do not have effective photophysical properties.

The bound metal metallized porphyrin art teaches that, by binding different metals to porphyrins at the core (to which the metals are so bound at the porphyrin core), different photophysical and other properties can be obtained by different bound metal(s)-porphyrin(s) structures.

To bind the metal to core of the porphyrin, the desired bound metallized porphyrins (including ZnPorphyrins) are synthesized under aggressive conditions. Reported conditions often include refluxing selected porphyrin with a suitable soluble metal salt or metal complex in appropriate organic solvents (such as methanol, dimethylformide, dimethylsulfoxide, and others) at temperature ranges typically from about 50° C. to 70° C. to over 100° C.

All within the metallized porphyrin art follow that synthesis art and do not work metal-porphyrin alternatives other than stable metal bound at porphyrin core.

Thus, for preparation for solar, sensing, bactericide or other application targeted for metallated porphyrin, rather than starting with metal alone or porphyrin alone, the art starts with bound metallized porphyrins made by aggressive methods.

However, the rigid structures of conventional metal-porphyrin compounds are not an active form complex for therapeutic application in dark conditions, even if in solution.

There is a need for next-generation of bactericides that avoid or reduce likelihood of developing bacterial resistance.

Also, there is a need for antibacterial and other therapy agents that are effective in light conditions, as well as dark, and capable to attack target cells multiple ways.

There is also need for improved water soluble, non-toxic, noninvasive, and low cost effective treatment compositions.

There is an additional need for new multifunctional treatment solutions which possesses antibacterial and PDT properties, including need for single dose or reduced dosage level compositions with high photodynamic antimicrobial efficiencies that can successfully eradicate antibiotic-resistant bacteria without causing development of additional resistance.

There is need for medically useful PSs with high antimicrobial photo-efficiency, specificity, and selectivity. In particular there is a need for PDI methods and PSs which are water-soluble, easily available, have high efficacy of killing microbes, low toxicity to the host, and have high singlet oxygen quantum yield.

Need also exists for materials, for example bactericides and medically useful PSs, which enable remote treating of the poor and needy in both developing and developed countries. Such materials need preparation without specialized and expensive synthesis equipment, skills or extensive training. There is thus a need for easy, simple, low cost preparations of highest grade of purity treatment compositions from commercial readily available components.

SUMMARY OF THE INVENTION

I have discovered treatments that reduce or avoid antimicrobial resistance and which have improved efficacy over certain conventional antimicrobials. I have found antimicrobials of high photo-efficiency, specificity, and selectivity. In addition, I have discovered multimodal compositions that treat cancer and bacteria, either simultaneously or in sequence.

I have discovered that various combinations at mild conditions of porphyrins and of hydrated metals (having a +2 ionic state with spatial and/or charge density attributes at molecular level at or near that occupied by Zn(II), defined herein below as "hMe(II)") can produce in situ forms of associations of hMe(II)+ porphyrin (where metal ions are loosely interacted with porphyrin) which possess better or different therapeutic properties than bound metal-porphyrin (e.g. where metal is aggressively bound to porphyrin core).

I have found that my inventive combination of metal with porphyrin is not rigidly stable, instead is unlike very stable bound metalloporphyrins prepared by conventional methods.

One example embodiment of this invention is combination of Zn(II) with free base meso-tetra(N-methyl-4-pyridyl) porphyrin tetrachloride (TMPyP) to form association complex in situ as loosely interacted resultant effect, which possesses better therapeutic properties than bound ZnTMPyP. In the sample variation of Zn(II) ions combined with TMPyP under inventive conditions shown in Examples herein:

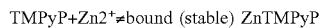

TMPyP+Zn2+≠bound (stable) ZnTMPyP

That is, when TMPyP+$Zn^{2+}$ are combined under mild conditions taught by this invention, resultant effect is that combination does not form a stable bound ZnTMPyP complex wherein Zn metal to TMPyP mole ratio would be 1:1. Mild conditions are unfavorable for stable binding of metal-to-porphyrin, instead the metal and porphyrin are loosely associated or loosely interacted, and in variations, in presence of residual excess metal or porphyrin, or excess of both.

Opposite to the art where stable bound metal-porphyrin complexes are prepared in extreme reaction conditions (refluxing the porphyrin with a suitable soluble metal salt in an appropriate organic solvent at relative high temperatures), gentle combination conditions of this invention do not provide high activation energies and do not create favorable conditions of reaction for fixed bonding of metal to porphyrin core to form stable metal-porphyrin with metal bound to porphyrin core.

Reactions for formation of stable metal bound metalloporphyrins require high activation energy. For illustration, elemental analysis of bound ZnTMPyP reveals it contains 1:1 Zn to porphyrin molecule mole ratio and it is a stable compound. Said stable compounds of bound ZnTMPyP (Zn:TMPyP mole ratio=1:1) are prepared by above described extreme reaction conditions involving refluxing porphyrin with a suitable soluble zinc metal salt in an appropriate organic solvent. ZnTMPyP complex (Zn:TMPyP mole ratio=1:1) is thus very stable at normal conditions of room temperature and atmospheric pressure. The only time zinc metal demetallates from the core of bound ZnTMPyP compound is when the complex (ZnTMPyP) is reacted at harsh conditions with strong acid such as hydrochloric acid. This indicates that zinc metal is tightly bonded to the core of the porphyrin.

Preferred compositions of this invention are loose combinations or association complexes of Me2+ ions with porphyrins wherein one or more Me2+ ions are loosely interacted and/or associated with (and not fixed bonded to) to a single porphyrin molecule, preferably two, or more than two, hMe(II) for each porphyrin. This produces (in situ) resultant effects whose structures are unknown but they possess therapeutic properties in dark and light conditions. For example, a variation of this invention includes loose combinations of Zn2+ ions and TMPyP wherein a single TMPyP molecule is loosely bound with Zn(II) ions (more than two) with a preferred zinc to TMPyP mole ratio of 2-to-1 to 3-to-1, even more preferably with an average metal to porphyrin mole ratio in the range of 2.85-to-1.

I have discovered a treatment and diagnostic system that combines features of photodynamic therapy with bacterial inactivation and antimicrobial photodynamic inactivation (aPDI). Variations of my discovery comprise multifunctional treatment and diagnostic systems. Said compositions slow or stop the progression of bacteria or certain cancer, or both, thus treating various malignancies and bacterial infections. I have also found that variations of said system are fluorophores and function for photodynamic diagnosis.

I have found methods for producing antibacterial agent in situ in (i) aerobic conditions and (ii) in anaerobic conditions and (iii) in absence of light and (iv) in presence of light. Furthermore, I found methods for generating singlet oxygen in aerobic environment. Variations of these methods and compositions used therein are multifunctional. They are capable of producing in situ reactive oxygen species and antibacterial agents under various reactions conditions, such as aerobic, anaerobic environments in presence of, or absence of light. They are capable, at the same time or different times or in rapid sequence, of switching sequence from one condition to another, for illustration, light to dark or aerobic to anaerobic. Variations comprise reactive oxygen produced in situ and non-toxic antibacterial agent in situ and are further multifunctional in being therapeutic and diagnostic.

As used in this Specification and the Claims,

"microbial inactivation means stopping or slowing growth of microorganisms; in one variation, "bacterial inactivation" means stopping or slowing growth of bacteria which may also stop or slow growth of other microorganisms present;

"microorganism" means a microscopic organism (especially a bacterium, fungus and/or virus) for illustration, not limitation, those selected from a group which consists of one or more of necrotizing fasciitis, archaea, Gram-positive and Gram-negative bacteria, bacterial spores, fungi, fungal spores, protozoa, algae, blood-borne parasites and viruses.

"adaptive resistance" means a microorganism's familiarity with structure or composition of antibacterial agent which reduces or eliminates capability for microbial or bacterial inactivation;

"singlet oxygen" means "($^1O_2$)";

"ROS" means reactive oxygen species comprising singlet oxygen or other chemotherapeutic species comprising oxygen;

"SOSG" means singlet oxygen sensor green detector;

"PSs" means nontoxic photosensitizers;

"DHN" used herein in this Specification as a singlet oxygen probe, not as a component of claimed treatment composition, means 1,5-dihydroxynaphthalene, the 1,5-isomer of dihydroxynaphthalene;

"PDT" means photodynamic therapy;

"photoactivation" means activation of subject composition with visible light;

"aPDI" means antimicrobial photodynamic inactivation;

"treatment" or "therapy" includes therapeutic effects by action of one or more agents toward remedial, beneficial, corrective, restorative, or healing results, as well as diagnosis.

"diagnosis" means fluoresces in aqueous medium having ability to be used for image guided photodynamic diagnostic applications, "fluorescence diagnosis" as part of "diagnosis" means generation of one or more optical results from a biological fluid or tissue of interest by reaction or other interaction with a diagnosis composition, wherein such diagnostic composition emits electromagnetic energy such as light at a certain wavelength when the composition or result of application of the diagnostic composition home to such fluid or tissue and such are illuminated by radiation of a selected wavelength;

"Bound" means coordinated, chelated and/or covalently bonded;

"Zincbacteriochlorin" means zinc covalently bound zinc bacteriochlorin, a class of porphyrin;

"TMPyP" means commercially available free base meso-tetra(N-methyl-4-pyridyl) porphyrin tetrachloride as shown in FIG. 10A;

"ZnTMPyP" or "bound ZnTMPyP" or "Zn(II)TMPyP" means commercially available meso-tetrakis(N-methyl-4-pyridyl) porphyrin with Zn metal stably bound into the core of porphyrin as shown in FIG. 10B (also known as with Zn metal bonded, coordinated, chelated and/or covalently bonded into the core of the porphyrin);

In connection with the claimed invention, as used in this Specification and the Claims, "Zn(II) ions" or "Zn(II)+", means loss of all electrons, in context of the fourth (and outermost) electron shell of Zn where Zn has only two electrons before coming to a closed n=3 shell, said loss of all electrons on said fourth shell, meaning Zn lost two negative charges, making it the ion Zn(II)+2;

Earlier research by me found that one or more embodiments of complexes of selected porphyrins with loosely bound Fe(III) "iron three" were not therapeutic unless composition also contains dihydroxynaphthalene or hydroxynaphthalene. Such was shown by example combination of TMPyP and 1,5-dihydroxynaphthalene with loosely bound Fe(III), which was not therapeutic in dark conditions unless also present was an adequate amount of activating agent such as hydrogen peroxide, as described in PCT/US2018/024338 (filed 26 Mar. 2018). This claimed invention addresses to eliminate third material.

A striking difference of this invention over my earlier research is that dihydroxynaphthalene or hydroxynaphthalene presence is not required for practice of this invention.

Also, basic chemistry of hMe(II)+ of this invention defined herein is no where near "comparable size or spatial geometry under reaction conditions near that of hMe(III)+" of earlier work where earlier efforts were related to "hydrated metal having a +3 ionic state with spatial attributes at molecular level at or near that occupied by Fe(III)". For illustration, basic chemistry of Zn(II) is not near comparable size or spatial geometry under reaction conditions near that of Fe(III)+, as shown by table below:

| Metal | Zn(II) | Fe(III) |
|---|---|---|
| Electronic configuration | [Ar]3d$^{10}$ | [Ar]3d$^{5}$ |
| Ionic radii (coordination type, tetrahedral) | 74 pm | 63 pm |
| Typical coordination numbers | 4 | 6 |
| Redox Potential-Standard Potential (volt) | −0.76 | −0.04 |

So further In connection with the claimed invention, as used in this Specification and the Claims, "hMe(II)" or "hMe(II)+" or "hydrated divalent metal having a +2 ionic state with spatial attributes and/or charge density at molecular level at or near that occupied by Zn(II)" means hydrated metals in +2 state which have comparable size and/or spatial geometry and/or similar charge density under combination or reaction conditions near that of Zn(II)+, where hMe(II) is to have a positive charge, for illustration, akin to that of "Zn(II)+"; and other metal +2 state variations which are capable of being loosely associated or interacted (via electrostatic attraction or otherwise) or loosely combined with one or more free base tetrakis Ar substituted porphyrins without bound metal or halide substitution at core; for avoidance of doubt, hMe(II) expressly includes divalent metals such as zinc(II), cobalt(II), iron(II), and manganese(II), and includes results of salts of zinc(II), cobalt(II), iron(II), and manganese(II) when subsequently hydrated for illustration Zinc sulfate heptahydrate;

"ArPP" or "ArPPh" means free base tetrakis aryl/alkyl (Ar) substituted porphyrin core without bound core metal or halide substitution at core, with variations comprising aryl/alkyl substituents at meso/beta positions, with variations same for substituents at meta positions and same or different for substituents at ortho/para positions, with variations being selected from an Ar group at meso positions consisting of hydroxyphenyl, N-alkylphenyl, carboxylatephenyl, sulfonatephenyl, alkyl pyridyl, and with variations being selected from an alkyl group consisting of alkyl, hydroxyalkyl, ammonium alkyl, and carboxylate alkyl, and their tautomeric and isomeric forms;

"ArPPhMe(II)" or "ArPPh+hMe(II)+" means one or more complex(ex) of metal ions and porphyrin without fixed bound metal or halide at porphyrin core (metal not covalently bonded, coordinated, chelated or stably fixed at core of one or more of porphyrins). One variation association complex comprises a combination of ArPPh with hMe(II) hydrated metal and resultant effect of combinations of ArPPh and Me(II) at mild conditions, such as at ambient temperature and atmospheric pressure, in aerobic or anaerobic conditions, wherein said hMe(II) metal is loosely associated, interacted and/or combined with one or more of said ArPPh (and wherein the metal is not covalently bonded, coordinated, chelated or fixed at core of porphyrin); also referred to in Specification and Claims as embodiment of associated metal metalloporphyrin complex or association complex;

"association complex" means combination where components are loosely interacted or combined (for illustration not limitation, via electrostatic or intermolecular attraction or orbital sharing or other means) for example porphyrin ArPPh with metal hMe(II)+", wherein metal is not bound, coordinated, chelated and/or covalently bonded into the core of the porphyrin; association complex includes molecular entity or entities resulting from loose association interaction involving one or more component molecular entities;

"TMPyP+Zn(II)" or "TMPyP/Zn(II)" means one embodiment of a claimed treatment composition of this invention as shown in FIG. 11 wherein hydrated Zn metal forms with TMPyP at mild conditions an association complex by being loosely interacted or combined (for illustration not limitation, via electrostatic or intermolecular attraction or orbital sharing or other means) with TMPyP, and wherein Zn(II) metal is not covalently bonded, coordinated, chelated and/or stably fixed to the core of the porphyrin;

"mild conditions" or "not at aggressive conditions" means moderate conditions such as at ambient temperature (and preferably less than about 50° C.) and at or near normal atmospheric pressure, preferably aqueous solution, and further preferably avoiding reflux of porphyrin;

"loosely interacted" or "loose association" means not covalently bonded, coordinated, chelated and/or stably fixed at core of one or more of porphyrins.

"random", in context of composition of combination or resultant effect, means altered to provide variations of (i) components, (ii) ratios of components, (iii) structures of molecular entities of components or (iv) association complex(es) or (iv) resultant effects or other changes to reduce chance of microbial adapting to or learning a fixed or single structure and developing adaptive microbial resistance;

"treatment composition" means one or more claimed variations of combinations of ArPP+hMe(II) and resulting effect produced, with or without presence of unreacted residual components, or other result of combination of ArPP and hMe(II);

"non-toxic chemotherapeutic agent" of this invention means one or more composition, reactants, reactions, or resultant effects or products of treatment composition (ArPP and hMe(II)) which may comprise ROS, and antibacterial agent produced in situ.

"in situ", in context of combination of variations of ArPP with hMe(II), means examining the reaction products, mixtures or other combination results, regardless of where or order combination or result occurs, for illustration, not limitation in a test tube or contact with mammalian tissue or fluid examining result exactly in place where result occurs.

"multifunctional" or "multimodal" or "capable of multifunctional activities" means composition or method of this invention which has one or more features selected from the group consisting of the following: (a) has capability to attack cells, either of same or different types, in same or proximate locale or presence, and in multiple ways, (b) is antibacterial agent in aerobic or anaerobic environment; (c) in absence of visible light in aerobic conditions, it produces antibacterial agent in situ, (d) in the presence of visible light irradiation, it produces $^1O_2$ in aerobic conditions, and antibacterial agent in aerobic conditions and anaerobic conditions; (e) in presence of or absence of light, it produces in situ reactive oxygen species such as singlet oxygen ($^1O_2$), (f) it has antibacterial properties, shown for illustration, by inhibiting the growth of E. coli in aerobic environment in both the presence and absence of light, (g) it has anticancer properties, shown for illustration, by inhibiting the growth of MCF-7 breast cancer cells in aerobic environment in the presence of light, (h) treatment or diagnosis is effective by a single dose or repeated doses are tolerated, or (i) it fluoresces in aqueous solution with potential for photodynamic diagnosis applications.

I have now discovered multifunctional compositions comprising variations of association complex(es) of combinations of porphyrins ArPPh and hydrated metals hMe(II).

Most surprisingly, I have discovered treatment composition that possesses great antibacterial properties in the dark, particularly against E. coli bacteria, in aerobic conditions, in the absence of light. Also, I found the treatment composition possesses great antibacterial properties, particularly against E. coli bacteria in aerobic, in presence of light.

I have now also discovered treatment compositions of this invention that, under visible light irradiation, produce $^1O_2$, and antibacterial agent in situ in aerobic conditions.

And surprisingly, the same treatment compositions also produce antibacterial agent in situ in anaerobic conditions.

I have now discovered compositions and methods of generating in situ reactive oxygen species, including without limitation, singlet oxygen ($^1O_2$), antibacterial agent, or combinations thereof, by use in aerobic or anaerobic environment in presence of light, or absence of light. These claimed compositions and methods are multifunctional, as further described herein.

I have unexpectedly found a method to adapt and use the treatment compositions to selectively produce one reactive oxygen species over others by varying concentration of hMe(II) ions in the treatment composition comprising also porphyrins ArPPh. The treatment compositions are highly soluble in an aqueous environment due to their ionic nature and do not form any aggregates at preferred concentrations in aqueous environments.

Also, I found the treatment composition fluoresces in aqueous solution to a reasonable extent so that they can be used for photodynamic diagnosis.

I further found the treatment composition possesses great photodynamic therapy properties, particularly against MCF-7 breast cancer cells in aerobic, in presence of light.

Treatment can be by a single dose of composition and in other variations, repeated doses are tolerated.

Other features and advantages of the invention will be apparent from the following detailed description, examples, drawings and claims.

BRIEF DESCRIPTION OF THE DRAWINGS

FIG. 1 shows in vitro effects on B2L21 E. coli under dark conditions of a preferred variation of claimed treatment composition (TMPyP+Zn(II)) at FIG. 1D compared against control (no addition) FIG. 1A and various components of treatment composition TMPyP FIG. 1B and Zn(ii) ions FIG. 1C.

FIG. 2 shows in vitro effects on B2L21 E. coli under dark conditions of a preferred variation of claimed treatment composition (TMPyP+Zn(II)) at FIG. 2C compared against control (no addition) FIG. 2A and conventional bound ZnTMPyP FIG. 2B.

FIG. 3 shows in vitro effects on B2L21 E. coli under dark conditions of a preferred variation claimed treatment composition (TMPyP+Zn(II)) at FIG. 3E compared against control (no addition) FIG. 3A, ampicillin FIG. 3B, chloramphenicol, FIG. 3C, and levofloxacin FIG. 3D.

FIG. 11 is a drawing of one simulated embodiment of claimed treatment compositions, wherein FIG. 11 shows TMPyP+Zn(II) formed by association of TMPyP with loosely interacted or combined Zn(II) ions which are not covalently bonded or otherwise bound to core of porphyrin, different and opposite to FIG. 10B.

FIG. 12 shows in vitro effects on B2L21 *E. coli* of various divalent hMe(II) (a) without presence of porphyrin TMPyP or (b) in combination with of porphyrin TMPyP under either (i) dark conditions (first and third columns from left) or (ii) light conditions (second and fourth columns from left), compared against control of porphyrin TMPyP alone without metal, also in dark or light.

FIG. 12 evaluated iron(II) row FIG. 12B, manganese(II) row FIG. 12C, cobalt(II) row FIG. 12E, and zinc (II) row FIG. 12D, each without presence of porphyrin TMPyP (first and second columns from left) and each with presence of porphyrin TMPyP (third and fourth columns from left) against control porphyrin TMPyP only (without metal) row FIG. 12A.

DETAILED DESCRIPTION OF THE INVENTION

Figures 4A, 4B, 4C, 4D, 4E:
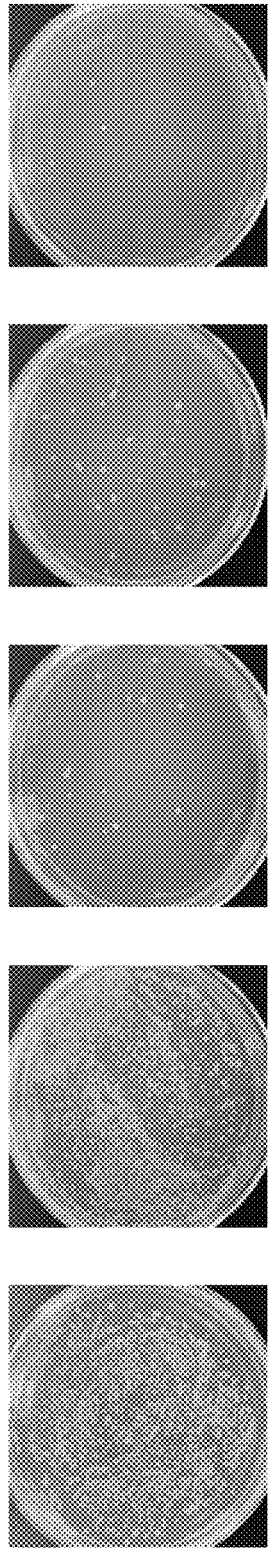
FIG. 4 shows in vitro effects on B2L21 E. coli under visible light irradiation of a preferred variation claimed treatment composition (TMPyP+Zn(II)) at FIG. 4E compared against control (no addition) FIG. 4A and various components of treatment composition TMPyP FIG. 4C, and Zn(II) ions FIG. 4B and against conventional bound ZnTMPyP FIG. 4D.

I have discovered, as one embodiment of this invention, a treatment composition comprising (a) a combination of (1) one or more free base tetrakis aryl/alkyl (Ar) substituted porphyrin core without bound core metal or halide substitution at core, wherein aryl/alkyl substituents are at meso/beta positions, are same for substituents at meta positions and same or different for substituents at ortho/para positions, are selected from an Ar group at meso positions consisting of hydroxyphenyl, N-alkylphenyl, carboxylatephenyl, sulfonatephenyl, alkyl pyridyl, and are selected from an alkyl group consisting of alkyl, hydroxyalkyl, ammonium alkyl, and carboxylate alkyl, their tautomeric and isomeric forms, and (2) one or more hydrated metal wherein metal has +2 oxidation state (hMe(II)), preferably with spatial attributes at the molecular level at or near that occupied by Zn(II) and (b) one or more resultant effects at mild conditions of combinations of one or more (a)(1) porphyrin and one or more said metals, wherein said (a)(2) metal is loosely interacted (not covalently bonded) with one or more of said porphyrins.

The term "resultant effect" is used in the Specification and Claims to mean any of association complex formed by interaction or other association of molecular entities from components of said combined above (a)(1) porphyrin and above (a)(2) hydrated +2 metal, either alone or with components present in mammalian tissue or fluid. Thus, one variation of resultant effect as association complex may be a molecular entity resulting from loose association involving one or more component molecular entities from combination of (a)(1) porphyrin and (a)(2) hydrated +2 metal of said composition, either alone or with components present in mammalian tissue or fluid. In another variation, resultant effect produced in situ also comprises reactive oxygen species (ROS), particularly singlet oxygen.

In one variation, treatment composition of this invention comprises free base tetrakis Ar substituted porphyrin core without bound metal or halide substitution at core, having alkyl pyridyl substituent at meso positions combined with +2 hydrated metal ion(s) for making resultant effect, and a one preferred variation thereof, said porphyrin core is meso-tetra(N-methyl-4-pyridyl)porphyrin tetrachloride without metal or halide substitution or bonding at core, and said metal hMe(II) is selected from the group consisting or of one or more of Zn(II), Co(II), Fe(II), and Mn(II). In one preferred variation, Zn(II) sulfate in aqueous solution is present.

When a variable association complex formed by association of molecular entities from components is desired as an effective treatment, one embodiment of a composition of this invention is prepared by combining ArPP and hMe(II)+ in presence or absence of light in aerobic and anaerobic environment or any sequence or combination of said conditions, and if variations are desired to reduce chance of microbial adaptive resistance, then combine with selected adjustments to cause variations or random other changes to reduce chance of microbe adapting to or learning a fixed or single structure and developing adaptive microbial resistance.

When singlet oxygen is desired as a treatment, one embodiment of this invention produces singlet oxygen in situ in presence of visible light and in aerobic condition, while yet other embodiments of this invention provides other treatments in presence of visible light and in aerobic condition by combining ArPP and hMe(II)+ in light and aerobic conditions.

In an embodiment of this invention important to achieve targeted results, I have discovered that if the amount of (a)(2) hydrated metal ions is increased or decreased in relation to combined amounts of said (a)(1) porphyrin or if one or more Me(II) is selected from the group consisting or one or more of Zn(II), Co(II), Fe(II), and Mn(II), then relative amounts of (i) molecular entities combined and produced resultant effects such as multiple association complexes formed by differing associations of molecular entities from differing components and/or (ii) singlet oxygen formed can be changed in a manner whereby one or more preferred resultant effect is achieved.

I have discovered that, by changing the amount of hydrated metal present relative to porphyrin, the relative interaction or association ability of one or more other components of the combination can be changed, for illustration, enhanced interaction in the instance of achieving a desired target result of *E. coli*'s inactivation by treatment composition. This is surprising, and it is not certainty whether such changes in relative interactions I found are caused by impact on association stability, stereochemistry or other characteristic of the combination or resultant effect. As evidenced by Examples herein, I found that in some instances decreases of concentration of metal ions increase level of certain interactions.

I have also found embodiments of this invention that have multifunctional activity. That is, I have found multifunctionality can be determined by changing ratios of combinations of (a)(1) porphyrin (without metal bound to porphyrin core) and (a)(2) hydrated +2 metal ions. For illustration, not limitation, in one variation, multifunctional compositions can be made by combining (a)(1) porphyrins selected from group consisting of meso-tetrakis(N-methyl-4-pyridyl) porphyrin tetrachloride (TMPyP) and (a)(2) of hydrated Zn(II) sulfate with (b) resultant effect comprising association complex formed by association of molecular entities from components and singlet oxygen. The resultant effect with association complex formed by association of molecular entities from components produced in situ has multifunctional activity for certain treatments, being effective as antimicrobial in absence of or presence of light and either, or both, aerobic and anaerobic conditions and yet for cancer cell damage or kill, the presence of light and aerobic conditions are required.

In above cited combination of (a)(1) porphyrin as TMPyP and (a)(2) of hydrated Zn(II) sulfate with (b) resultant effect including singlet oxygen and association complex, I found that the mole ratio of Zn(II) ions can be increased or decreased in relation to moles of said porphyrins to change of resultant effect ratios produced of said singlet oxygen and said association complex formed by association of molecular entities from components.

That discovery enables a specific variation of an embodiment of a composition of this invention whereby TMPyP is combined with hydrated Zn(II), where mole ratios of Zn(II) ions combined with TMPyP preferably is in mole ratio of (i) Zn(II) ions to TMPyP within range of 2:1 to 3:1, more preferably an average of 2.85:1, wherein final concentration of hydrated Zn(II) can be adjusted and selected to achieve desired level of *E. coli*'s inactivation and also of singlet oxygen production.

One preferred variation of this embodiment is a combination comprising TMPyP and Zn(II) ions at mole ratios of 2.85 for initial Zn(II) to 1 TMPyP wherein combined is TMPyP as $1.10\times10^{-9}$ moles of TMPyP equivalent of $9.0\times10^{-7}$ g (Mwt for TMPyP—820.64) and hydrated Zn(II) ions in combined at an initial amount of $3.13\times10^{-9}$ moles obtained from equivalent to $9.0\times10^{-7}$ g (Mwt for $ZnSO_4$—287.53) but Zn(II) is adjusted to an amount within the range of $2.61\times10^{-7}$ M to $4.17\times10^{-6}$ M to adjust the rate of *E. coli* activation by resultant effect association complex TMPyP+Zn(II) to produce greater quantities of one or more preferred chemotherapeutic result effects selected from association complex formed by association of molecular entities from components and singlet oxygen.

Thus in a specific embodiment, I have discovered that the treatment composition comprising TMPyP and hZn(II)+ in aqueous solution provides a composition and various methods to stop or kill the growth of *E. coli* bacteria by a single dose or reduced repeat doses, in presence of and absence of visible light, and is effective as treatment composition in aerobic as well as anaerobic environments and said treatment system produces singlet oxygen in aerobic conditions in presence of visible light.

Also, in a specific embodiment, I have discovered that the treatment composition comprising TMPyP and hZn(II)+ in aqueous solution provides a method to stop or kill the growth of cancer cell (for illustration, not limitation MCF-7 breast cancer cells) by a single dose or reduced repeat doses in presence of visible light, effective as treatment composition in aerobic environments and said treatment system produces singlet oxygen in aerobic conditions in presence of visible light.

Thus TMPyP and hZn(II)+ in aqueous solution is effective simultaneously as an antibacterial agent and photodynamic therapy agent effective against bacterial infections and cancers by a single dose, or reduced repeat doses, in absence of light or in presence of visible light, effective as treatment composition in aerobic environments and said treatment system produces singlet oxygen in aerobic conditions in presence of visible light and thus effective in light against cancer.

Unlike many prior art chemotherapy and antibacterial agents, I have found, as confirmed by the Examples herein, that claimed combinations and methods of this invention can be effective in a relatively short period of time, and in a non-toxic manner. I have also found, as confirmed by the Examples herein, that combinations and methods of this invention for preparation of treatment and for its dispensing for application require less than one (1) hour. Such preparation, dispensing and application can be substantial completed, as demonstrated by Examples below, in less than twenty (20) to thirty (30) minutes, and in certain instances about fifteen (15) minutes. Such short application time enables rapid, effective field treatments, and may include certain diagnosis, in locations at which any kind of treatments or diagnosis were heretofore prohibited.

The treatment compositions of the present invention are thus useful in general, in the manner known in the art for treatment of bacteria or of cancers or for fluorescence diagnosis. For use in in vivo treatment or diagnosis of malignancies or bacterial infections treated systemically, the compositions are typically administered by injection, and permitted sufficient time to home to the malignancies or infections or infective agents. Injection may be intravenous, subcutaneous, intramuscular, or intraperitoneal, and other administration may be orally, in some instances, or by other means of another approved mode of pharmaceutical administration. Injectable solutions can be prepared in conventional forms, preferably with water as excipient.

In one embodiment, the mole ratio of (a)(1) porphyrin and (a)(2) hydrated +2 metal is not 1-to-1 and excess residual of (a)(1) porphyrin or (a)(2) hydrated +2 metal or of both are present. In one variation, resultant effect produced in situ has more than one possible association by altering selected components of (a)(1) porphyrins or (a)(2) hydrated +2 metals, or ratios of (a)(1) porphyrin to (a)(2) hydrated +2 metal, which can be altered to reduce chance of developing adaptive microbial resistance by altering selected ratios of (a)(1) porphyrin to (a)(2) hydrated +2 metal. In other variations, concentration ratios of (a)(1) porphyrin to (a)(2) hydrated +2 metal are adjusted to achieve target rate of inhibition of growth of bacteria with or without photoactivation of the (a)(1) porphyrin. In preferred variations said mole ratio metal-to-porphyrin is in range of 1 to 2.00 up to 3.00. In more preferred variations said mole ratio of (a)(1) porphyrin to (a)(2) hydrated +2 metal is in range of 1 to 2.85.

I have found compositions of this invention are capable of multifunctional activities, wherein ratios of (a)(1) porphyrin to (a)(2) hydrated +2 metal are adjusted to determine level of a selected target activity of one or more of resultant effect capable multifunctional activities.

I have found embodiments of combinations of (a)(1) porphyrin and (a)(2) hydrated +2 metal in aerobic or anaerobic conditions with or without added light or other separate activator produces resultant effect effective for treatment of bacteria.

In a process embodiment of this invention, a method to produce antibacterial association complex formed by association of molecular entities from components and (b) singlet oxygen in situ is provided as resultant effect of combining ArPP and hMe(II)+. In one variation, optionally the mole ratio of hMe(II)+ is increased or decreased in relation to mole ratios of ArPP to selective produce greater amount of antibacterial association complex over other resultant effects. Specific enablement of methods of preparation of solutions of components of treatment compositions are taught by the Examples below.

Other embodiments of combinations of one or more (a)(1) porphyrin and one or more (a)(2) hydrated +2 metal in aerobic conditions with added light or other activator (such as peroxide) produce one or more resultant effect comprising singlet oxygen or combinations thereof effective for treatment of bacteria or cancer or both in sequence or simultaneously. In a specific example variation, (a)(2) hydrated +2 metal is hydrated Zn(II) and concentration of said (a)(2) hydrated Zn(II) is adjusted and selected to achieve desired level of one or more of bacteria inhibition and singlet oxygen production. In one preferred manner to make combinations of this invention, one or more of hMe(II) and one or more of porphyrin are selected and mole ratios of said total porphyrin(s) and total metal(s) ions are adjusted and combined for effective single dose or for repeat dose enablement.

I have found that embodiments of compositions of this invention multifunctional activity in aerobic or anaerobic conditions for diagnosis or treatment of bacteria and cancer, the level of activity being determined by (i) selection of one or more (a)(1) porphyrins and one or more (a)(2) hydrated +2 metal combination, as well as concentration ratios of total of one or more of (a)(1) porphyrins and total of one or more (a)(2) hydrated +2 metals and (ii) presence of light or absence of light, except where cancer treatment requires or is enabled by presence of light and aerobic conditions or separate activator.

A preferred variation of a composition of this invention comprises TMPyP as (a)(1) porphyrin and Zn(II) ions as (a)(2) hydrated +2 metal at average mole ratios of 1 TMPyP to 2.85 Zn(II) ions in presence of visible light and in absence of light. In a variation, (b) resulting effect comprises in situ produced complex(es) of Zn2+ ion and TMPyP wherein a single TMPyP molecule is loosely bound with one or more Zn2+ ions, preferably more than two, with a zinc to TMPyP mole ratio of 1:2.85. In another specific variation, resultant effect comprises (ii) residual of (a)(1) meso-tetrakis(N-methyl-4-pyridyl) porphyrin tetrachloride and of (a)(2) of hydrated Zn(II) sulfate and (ii) primarily combination association complex of said porphyrin and hydrated Zn(II) sulfate.

I have discovered a method to make treatment compositions wherein concentrations and mole ratios of one or more of said porphyrins and one or more of said metal ions are adjusted for effective single dose or for repeat dose enablement (a) against bacterial infections as an antibacterial agent in aerobic or anaerobic conditions and in absence of light or in presence of visible light, or (b) simultaneously or sequentially in aerobic conditions (1) against bacterial infections as an antibacterial agent and (2) against cancers as photodynamic therapy agent in presence of visible light, wherein singlet oxygen is produced. In one variation, final concentration of (a)(2) metal ions related to (a)(1) porphyrin is selected to achieve target rate of inhibition of growth of bacteria with or without photoactivation of the porphyrin. In another variation, I found that I can make 1.(b) resultant effect capable of multifunctional activities by adjusting ratios of (a)(1) porphyrin to (a)(2) hydrated metal to determine level of a selected target activity of one or more of (b) resultant effect capable multifunctional activities. Also, a treatment composition can be made in a manner wherein amount (a)(2) metal ions is increased or decreased in relation of said (a)(1) porphyrin to change relative amounts of (i) said association complex formed by association of molecular entities from components (a)(1) porphyrin and (a)(2) metal ions and of (ii) singlet oxygen species produced in situ.

In one embodiment, an antibacterial agent can be formed in situ by association of molecular entities from components (a)(1) porphyrin and (a)(2) metal ions with resultant effect 1.(b) of claim 1 comprising an association complex and singlet oxygen. In a variation of such formation of a complex effective as an antibacterial agent, I have found that if the amount said (a)(2) metal ions is increased or decreased in relation of said (a)(1) porphyrin such changes relative amounts of (i) said antibacterial complex formed by association of molecular entities from porphyrin and metal ion components and of (ii) singlet oxygen species. A preferred treatment is an antibacterial agent formed in situ by association of molecular entities or complex of (a)(1) free base tetrakis Ar substituted porphyrin core without bound metal or halide substitution at core but having alkyl pyridyl substituent at meso positions combined with (a)(2) +2 hydrated metal ions, with or without production of singlet oxygen. Inhibition of growth of bacteria with or without photoactivation of (a)(1) porphyrin can be adjusted by adjusting concentration of (a)(2) metal ions (a)(2) relative to (a)(1) porphyrin until target level of inhibition is achieved.

In an aerobic or anaerobic environment, a combination of ArPP and hMe(II) in absence of visible light or presence of visible light can inhibit growth of bacteria and other microorganims. Such combination is effective for bacteria selected from a group which consists of one or more of necrotizing fasciitis, Gram-positive and Gram-negative bacteria, and bacterial spores, and said treatment can simultaneously or sequentially be effective against viruses, archaea, fungi, fungal spores, protozoa, algae and blood-borne parasites.

Singlet oxygen can be produced in situ in aerobic environment by combining ArPP and hMe(II) in presence of light. Thus cancer can be damaged or killed by treating it with combination of ArPP and hMe(II) in presence of light in an aerobic environment. Thus combination ArPP and hMe(II) in presence of light can inhibit bacteria and simultaneously or sequentially damage or kill cancer in an aerobic environment. hMe(II) concentrations can be adjusted and selected to achieve desired level of bacteria inactivation and singlet oxygen production.

In another important variation, ratios of (a)(1) porphyrin to (a)(2) metals can be adjusted to reduce adaptive bacterial resistance. Also, in one variation shown in Examples, by combining meso-tetra(N-methyl-4-pyridyl) porphyrin tetrachloride and Zn(II) sulfate in aqueous solution in presence of visible light in aerobic environment, singlet oxygen can produced to damage or kill cancer or inhibit bacteria, or treat both cancer and bacteria, by a single dose or resistance enabled repeat low dose.

In a specific embodiment, a method for image-guided photodynamic therapy by using TMPyP+Me(II) to fluoresce in aqueous media and varying fluorescence intensity of TMPyP+Me(II) by varying the presence of Me(II) ions is found. For illustration, the rate of photooxidation of TMPyP+Zn(II) can be varied by varying concentration of Zn(II) metal ions in relation to TMPyP, whereby (a) at lower concentration of metal ions, preferably in range of 0.075 ppm, metal ions associate with TMPyP as a specific form of active complex with which can effectively produce singlet oxygen, preferably 1.45 times higher than concentrated zinc ions solution, and (b) at higher concentration of metal ions, preferably in range of 0.150 ppm, wherein the association, structure or form of porphyrin/metal complex is different than lower concentration (a), and more efficient in quenching excited states of porphyrin leading to decrease in production of singlet oxygen.

In one embodiment of compositions of this invention, an antimicrobial agent is formed in situ as association complex comprising varying or random amounts or association of components or molecular entities from components from which said agent is formed. In a variation effective to reduce developing microbial resistance over that of single antimicrobial structure, random or adjustable structures or associations of combination of components and of resultant effects are produced in situ, wherein random or adjustable composition structures or associations reduce possibility that microorganisms develop adaptive resistance to a single structure or association. In one variation, antibacterial agent having reduced adaptive resistance is made varying or having random amounts or associations of free base tetrakis aryl/alkyl substituted porphyrin core without bound metal or halide substitution at core and hydrated metal wherein metal has +2 oxidation state, and resultant effects of such amounts or associations. In a specific embodiment, a method to reduce chance of developing bacterial resistance to a single antibacterial structure is by varying selected ratios of one or more (a)(1) porphyrin to one or more (a)(2) metal ions in a treatment composition of comprising combination of one or more (a)(1) porphyrin and one or more (a)(2) metal ions and (b) resultant effect of said combination produced in situ by combination of various or random (a)(1) porphyrin and (a)(2) metal ions in differing ratios for (b) resultant effect to have more than one random or selected structure or association, which random or select structures or associations reduce chance of bacteria developing adaptive bacterial resistance to a single structure or associated of selected ratio of (a)(1) porphyrin and (a)(2) metal ions.

EXAMPLES

Materials, Apparatus, Stock Solutions and Methods

Materials

All chemicals were acquired from commercially available chemical vendors and used as received without further purification, except as noted. TMPyP and Zn(II)TMPyP (bound) were bought from Frontier Scientific Inc, USA. Zinc (II) heptahydrate was purchased from Flinn Scientific Inc, USA. Ultrapure water $H_2O$ (18.2 MO) was obtained from a U.S. Filter Corporation deionization system. USA. Isopropanol (2-propanol) was received from VWR Analytical, USA, and $D_2O$ and acetonitrile, from Sigma-Aldrich, USA. Ampicillin and levofloxacin were purchased from Sigma-Aldrich, USA. Chloramphenicol was obtained from Tokyo Chemical Industry, USA. Luria-Broth (LB broth) was acquired from Sigma Aldrich, USA. Iron(II), Cobalt(II) and Manganese (II) salts were acquired from Sigma-Aldrich, USA.

Apparatus

All photosensitization experiments were carried out on a Rayonet Chamber reactor equipped with sixteen 57505750 Å lamps (The Southern New England Ultraviolet Co, USA, model RPR-100). Blue continuous-wave ("CW") laser (447 nm, 20 mW, 2.0 mm beam diameter), green CW laser (532 nm, 20 mW, 2.0 mm beam diameter), and CW laser (655 nm, 100 mW, Model: MRL-III-655-100 mW 15060452) purchased from Dragon Lasers Co., China were used for photosensitization reactions. Agilent 8453 single beam diode array spectrometer (Agilent Technologies, USA, model 8453) was used for recording ultraviolet-visible (UV-Vis) spectra at room temperature. Fluorescence spectra were recorded by using a Perkin-Elmer LS-55, Fluorescence Spectrometer (Perkin-Elmer, USA) at room temperature under normal atmospheric conditions.

Stock Preparation and Methods

Standard solution of TMPyP ($1.00 \times 10^{-3}$ M), (bound) ZnTMPyP ($1.00 \times 10^{-3}$ M) and zinc (II) sulfate ($1.0 \times 10^{-3}$ M) were prepared from commercial sources in ultra-pure water at room temperature under normal atmospheric conditions.

Ampicillin ($1.00 \times 10^{-3}$ M) and chloramphenicol ($1.00 \times 10^{-3}$ M) were prepared in ultra-pure water at room temperature under normal atmospheric environment. Levofloxacin was prepared in $CH_3CN:H_2O$ (9:1, v/v) at room temperature under normal atmospheric conditions.

DHN is used herein as a singlet oxygen probe, not as a component of the treatment composition. DHN ($1.0 \times 10^{-2}$ M) stock solution was prepared in a $CH_3CN:H_2O$ (9:1, v/v) mixture solvents at room temperature under normal pressure.

For preparing a typical experimental solution of example of variation of claimed composition, microliter amounts of a stock solution of zinc metal ion solutions (5.57 μL of $1.0 \times 10^{-3}$M) were added into a cuvette containing 3.0 mL of aqueous solution of TMPyP ($3.67 \times 10^{-7}$ M) and, where applicable, DHN ($1.2 \times 10^{-4}$ M). Quartz cuvettes with 1 cm path-length and 3.0 mL volume were used for all measurements. Solutions of Iron(II), Cobalt(II) and Manganese (II) were prepared in similar manner for evaluation Example 10.

For singlet oxygenation experiment, a 3.0 mL solution of DHN ($1.2 \times 10^{-4}$ M) and TMPyP ($3.67 \times 10^{-7}$ M) was prepared by mixing 36 μL of $1 \times 10^{-2}$ M of DHN standard solution and 1.10 μL of $1 \times 10^{-3}$ M of TMPyP standard solution with ultrapure water at room temperature in an open atmosphere. Singlet oxygenation of sample was conducted in a Rayonet photoreactor for approximately 10 min at 28° C. and the photooxidation of DHN was monitored by recording a decrease in UV-Vis absorption of DHN at 300 nm for 10 min in 2 min intervals. The effect of zinc metal ions on singlet oxygen generation was studied similarly except with the addition of microliter amounts of Zn(II) ions ($1 \times 10^{-1}$ M) into a DHN/TMPyP aqueous solution.

E. coli (BL21) bacteria was used as a model prokaryote to determine the efficacy of the inventive treatment composition to kill bacteria. The effect of inventive composition as well as each individual component of the composition were all tested to determine the effect each on the growth of *E. coli* bacteria. The procedure described in Herschmann, R. J. et al (2019) "Effect of toxic metal ions on photosensitized singlet oxygen generation for photodegradation of polyaromatic hydrocarbon derivatives and inactivation of *Escherichia coli*" Photochemistry and Photobiology 86, 890-894, was followed. The bacterial cultures were grown in an incubator in Luria-Broth (LB)—Lennox formulation at 28° C. with shaking at 250 rpm. Once the cells reached the beginning of their exponential growth phase ($A_{600}$=0.2), one milliliter aliquots were removed and centrifuged. The resulting pellets were washed once with sterile water and then resuspended in 500.0 µL of sterile water. The resuspended bacteria were mixed with 200.0 µL of stock solutions of the components or the multifunctional was selected for testing at 0.3 ppm for all components of the composition. The experimental samples were irradiated in a Rayonet photoreactor for 10 minutes or covered and kept in the dark for 10 minutes. Controls were prepared using 200.0 µL of sterile water were also prepared with one control being irradiated and the other control being kept in the dark. All samples were then briefly vortexed to thoroughly mix samples, and 20.0 µL aliquots of each sample were evenly spread using standard techniques over individual LB agar petri dishes. The plates were inverted and incubated at 28° C. for 48 hours. Results are reported as observed effects of the composition and each component of the composition on the inhibition of the growth of *E. coli* on the plates.

For breast cancer cells experiment, a stored sample was taken and incubated for 3 to 5 minutes until room temperature. 5 mL of supplemented medium was placed in a 15 mL centrifuge tube. The contents in the cryotube were transferred into the 15 mL centrifuge tube containing the 5 mL medium. This mixture was centrifuged for 5 minutes at 1000 rpm. The supernatant was removed, and 3 mL of the medium was added to the cells and mixed thoroughly. From this mixture, 1 mL was placed into three separate culture flasks with 11 mL of medium each. These flasks were placed in a humidified atmosphere of 32° C. and 5% $CO_2$. After incubation, cells were rinsed with PBS and aspirated. Cells were washed with trypsin, covered and placed in the incubator for five minutes. Solutions were then mixed with 4 mL of medium and subsequently transferred into a 15 mL centrifuge tube to be centrifuged for 5 minutes at 1000 rpm. The supernatant was then aspirated, and cells were re-suspended in 3-10 mL of medium. From here, 1 mL aliquots of this mixture were placed with 11 mL of medium in a new flask. Lastly, these flasks were placed in humidified atmosphere of 32° C. and 5% $CO_2$. An aliquot of the stock solution (i.e. 9.5 mL) was removed from the stock culture and combined with an appropriate amount of regular medium (i.e. 220.5 mL). After proper mixing the stock with fresh media, 3 mL of the mixture were placed in each of the wells in a 6-well plate. Using the manufacturer's protocol, a MTS assay was performed to assess cell proliferation and toxicity of the multifunctional treatment composition. The concentrations of inventive treatment composition and its individual components were 0.3 ppm, until adjusted. The proliferation(s) of cells were compared to a control of cells alone. The growth the control was standardized as 100% growth and the cell proliferation in the presence of the treatment composition was observed and reported on the bases of percent when compared to the control. Similar procedure was followed for light experiment where samples were irradiated in a Rayonet photoreactor for 10 minutes.

A fluorescence study of TMPyP and TMPyP with zinc (II) ions was prepared in 3 mL solutions. Each solution was prepared using ultrapure water prepared at room temperature and normal atmospheric pressure. A $1.0 \times 10^{-6}$M TMPyP and zinc (II) solution was prepared for the experiment. Fluorescence emission was measured upon excitation of each solution at 423 nm with an excitation slit width of 10.0 nm and an emission slit width of 12.0 nm.

The generation of singlet oxygen from claimed composition and variations of claimed treatment compositions was assessed in a series of tests in aerobic conditions under visible light irradiation. The observation of generation of singlet oxygen teaches that the claimed composition is of significance based clinical therapy wherein an abundant supply of singlet oxygen is required.

Example 1

In vitro effects of example variation of inventive treatment composition TMPyP+Zn(II) ions were tested under dark environment and are reported in FIG. 1. FIG. 1 shows the inhibition of *E. coli* growth after 48 hours.

That is, to determine the utility for treatment of bacteria of the claimed compositions in aqueous environment (which is also typical tumor environment), a solution of *E. coli* was mixed with the sample treatment composition in dark conditions under normal atmospheric environments and compared against other compositions.

A series of control reactions were conducted to determine if growth of *E. coli* bacteria can be inhibited under identical conditions against (i) no additions (FIG. 1A) or (ii) with TMPyP alone at 0.3 ppm (FIG. 1B) or (iii) with Zn(II) ions alone at 0.3 ppm (FIG. 1C) or (iv) with addition of invention composition TMPyP+Zn(II) of Zn(II) ions (0.15 ppm) and TMPyP (0.15 ppm).

In FIG. A, FIG. B and FIG. C, essentially no noticeable inhibition of growth of *E. coli* bacteria was observed at those experimental conditions.

As shown in FIG. 1 at FIG. 1D, complete inhibition of growth of *E. coli* was observed when TMPyP+Zn(II) ions were used (FIG. 1D). After 48 hours, a complete inhibition of *E. coli* was observed (FIG. 1D) when a half concentration of Zn(II) ions (0.15 ppm) and half TMPyP (0.15 ppm) was reacted with *E. coli* bacteria. Thus, the claimed composition has properties that slow or stop the progressions of bacteria.

Example 2

In vitro effects of inventive treatment composition TMPyP+Zn(II) ions were compared against bound ZnTMPyP and a control under dark environments. Results are reported in FIG. 2. which indicates relative inhibition of *E. coli* growth after 48 hours.

That is, to determine the efficacy and the utility of the claimed compositions, a comparison study was conducted where a solution of *E. coli* was reacted separately in dark conditions with bound ZnTMPyP and with example inventive treatment composition (TMPyP+Zn(II) ions), all under normal room temperature and pressure.

FIG. 2A shows growth of *E. coli* with no reactant and is used as a control.

As shown in FIG. 2B, the solution of bound ZnTMPyP at 0.3 ppm showed almost no inhibition of *E. coli* bacteria when contacted in dark aerobic conditions.

As depicted in FIG. 2C, an almost complete inhibition of growth of *E. coli* was observed when inventive composition TMPyP+Zn(II) ions at 0.3 ppm was contacted with *E. coli* bacteria also in dark aerobic conditions. Bound ZnTMPyP has been used to kill *E. coli* bacteria under light irradiation conditions only. When previously tested by others under dark conditions, bound ZnTMPyP was found not effective in killing E. coli bacteria under dark conditions as confirmed by this Example 2 and FIG. 2B results; no similar test evaluation by others of associations of unbound hMe(II) ions with porphyrins, such as inventive example TMPyP+ Zn(II), has been found.

Example 3

In vitro effects of treatment composition ampicillin, levofloxacin, and chloramphenicol under dark environments were tested against inventive example TMPyP+Zn(II) ions. Results are reported in FIG. 3 which indicates relative inhibition of E. coli growth after 48 hours.

That is, to determine the efficacy and the utility of the claimed compositions, a comparison study was conducted where a solution of E. coli was contacted in dark conditions separately with ampicillin, levofloxacin, and chloramphenicol and with example inventive treatment composition (TMPyP+Zn(II) ions), all under normal room temperature and pressure.

As shown in FIG. 3E, an almost complete inhibition of growth of E. coli was observed when example inventive treatment composition TMPyP+Zn(II) ions at 0.3 ppm was used with E. coli bacteria.

FIG. 3A shows growth of E. coli with no reactant and is used as a control.

Almost no inhibition of growth of E. coli was observed when the solution of E. coli was used to react separately with 0.3 ppm ampicillin (FIG. 3B), and 0.3 ppm chloramphenicol (FIG. 3C). In FIG. 3D substantial inhibition of E. coli's growth was observed when the E. coli solution was treated with levofloxacin with 0.3 ppm concentration (FIG. 3D).

In FIG. 3E, nearly a complete inhibition of E. coli bacteria was observed when the E. coli solution was treated with claimed composition TMPyP+Zn(II) with 0.3 ppm concentration. Therefore, the claimed composition at the experimental concentration is more effective and has the potential to be used for bacterial infections at low doses.

Ampicillin and chloramphenicol are not effective at low concentrations used. I estimated by calculation that if one uses 17 to 20 times higher concentration of commercial antibiotics ampicillin and chloramphenicol than the claimed composition, those levels would be effective against bacteria. Opposite thereto, use of low concentrations of one or more effective dose of inventive compositions allows avoidance of developing antibiotic resistance.

Example 4

In vitro effects of example inventive treatment composition (TMPyP+Zn(II)) on BL21 E. coli in aerobic conditions under visible light irradiation were tested and are reported in FIG. 4. FIG. 4 shows E. coli growth, monitored after 48 hours.

A series of control evaluations were conducted to determine if growth of E. coli bacteria can be inhibited under identical conditions against (i) light alone, no additions (FIG. 4A) or (ii) with Zn(II) ions alone at 0.3 ppm (FIG. 4B) or (iii) with TMPyP alone at 0.3 ppm (FIG. 4C) or (iv) with addition of invention composition TMPyP+Zn(II) of Zn(II) ions (0.15 ppm) and TMPyP (0.15 ppm).

To determine the utility for treatment of bacteria of the claimed treatment compositions, the treatment composition was tested to see if it inhibits E. coli bacteria.

In FIG. 4A, light alone showed very marginal inhibition effect of E. coli growth.

In FIG. 4B, Zn(II) ions alone at experimental concentration (0.3 ppm) showed almost no inhibition of growth of E. coli under irradiation conditions.

FIG. 4C confirms complete inhibition of growth of E. coli when E. coli solutions are treated with TMPyP and exposed to visible light. That is, FIG. C confirms prior art that TMPyP inhibits of E. coli growth. Per prior art reactive oxygen (singlet oxygen) produced from photosensitization reaction of TMPyP inhibits E. coli growth.

FIG. 4D shows inhibition of growth of E. coli when E. coli solution is treated with ZnTMPyP and exposed to visible light, confirming work by others to show reactive oxygen (singlet oxygen) produced from photosensitization reaction of bound ZnTMPyP inhibits E. coli growth.

Surprisingly, in FIG. 4E unbound TMPyP+Zn(II) ions the example variation of claimed treatment composition produces better results than FIG. 4D for bound ZnTMPyP or at least similar results.

As shown in FIG. 4E, near total inhibition of E. coli was observed with example variation of claimed treatment composition under visible light irradiation.

The data of claimed treatment composition can be viewed to show that it is even more effective in inhibiting the growth of E. coli bacteria compared to TMPyP alone or ZnTMPyP alone.

This data indicates that the treatment composition, TMPyP+Zn(II) is more efficient to form reactive oxygen species in presence of light, particularly singlet oxygen which is the key species for total inhibition of E. coli bacteria and treatment of cancer.

Example 5

Figure 5:
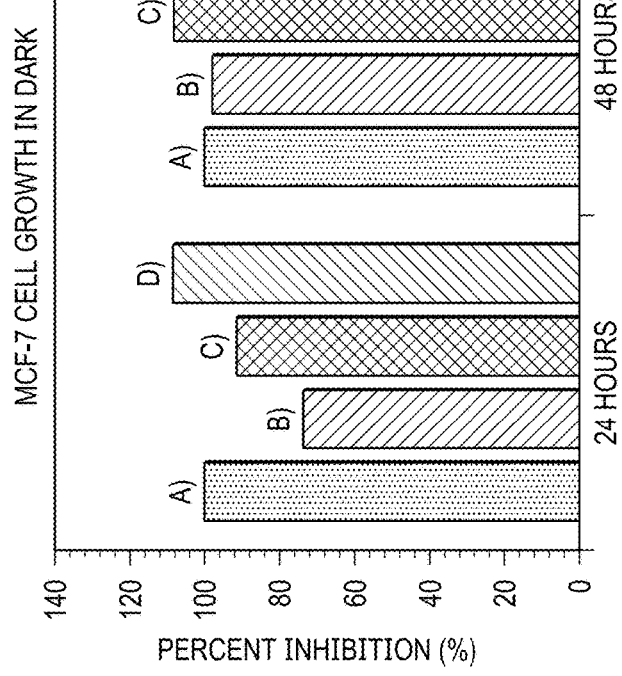
FIG. 5 shows in vitro effects on MCF-7 breast cancer cells under dark conditions of a preferred variation claimed treatment composition (TMPyP+Zn(II)) at FIG. 5D compared against FIG. 5A, FIG. 5B, and FIG. 5C various components of treatment composition.

In vitro effects of treatment composition (TMPyP+Zn(II)) on MCF-7 breast cancer cells in aerobic conditions under dark environments were tested and are reported in FIG. 5. FIG. 5 (left and right) shows the inhibition of MCF-7 breast cancer cells growth after 48 hours at various test conditions.

To determine the utility for treatment of cancers of the claimed treatment compositions, the treatment composition was tested to see if it inhibits MCF-7 breast cancer cells growth under dark conditions.

FIG. 5A shows the growth of MCF-7 breast cancer cells with no reactant and used as a control.

FIG. 5B shows Zn(II) ions alone at experimental concentration (0.3 ppm). Zn(II) ions showed no inhibition effect of MCF-7 breast cancer cells growth in aerobic and at dark conditions.

FIG. 5C shows TMPyP alone in dark. A very similar result was obtained when TMPyP was reacted with MCF-7 breast cancer cells in dark. As shown in FIG. 5C, TMPyP alone at experimental concentration (0.3 ppm) showed almost no inhibition of growth of MCF-7 breast cancer cells.

FIG. 5D shows that at normal room temperature and pressure under dark conditions the claimed treatment composition TMPyP+Zn(II) ions shows no inhibition of growth of MCF-7 breast cancer cells at the experimental concentration (0.3 ppm). Thus, the treatment composition is non-toxic to breast cancer cells in dark and remains so nontoxic unless it is triggered or continuously activated by light. However, the treatment composition, TMPyP+Zn(II) in dark conditions shows antibacterial property, particularly against E. coli. See FIG. 2.

Example 6

Figure 6:
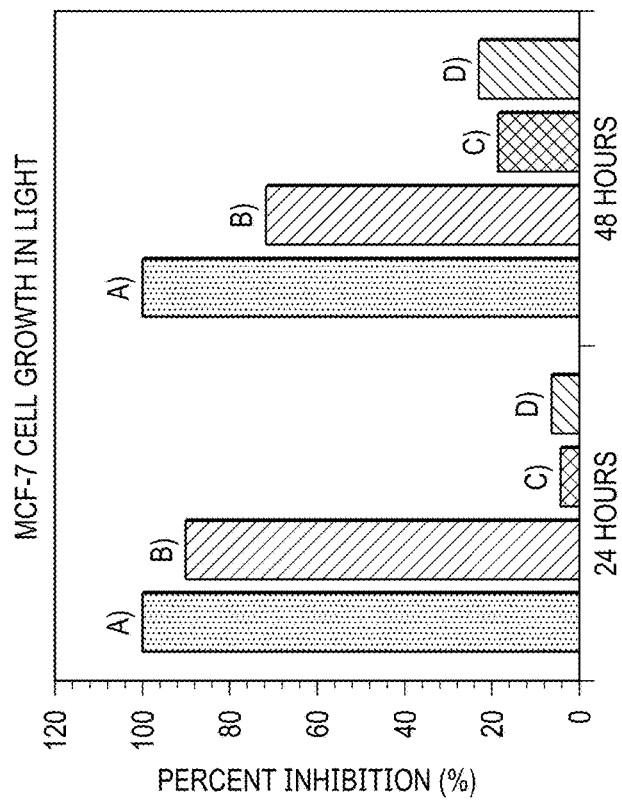
FIG. 6 shows in vitro effects on MCF-7 breast cancer cells under visible light irradiation of a preferred variation claimed treatment composition (TMPyP+Zn(II)) at FIG. 5D compared against FIG. 5A, FIG. 5B, and FIG. 5C various components of treatment composition.

In vitro effects of treatment composition (TMPyP+Zn(II)) on MCF-7 breast cancer cells in aerobic conditions under visible light irradiation were tested and are reported in FIG. 6, ad FIG. 6D (right and left).

FIG. 6 shows the inhibition of MCF-7 breast cancer cells growth after 48 hours, at various test conditions.

To determine the utility for treatment of cancers of the claimed treatment compositions, the treatment composition was tested to see if it inhibits MCF-7 breast cancer cells growth under visible light irradiation.

As depicted in FIG. 6A left and right, light alone showed no inhibition of growth of MCF-7 breast cancer cells.

FIG. 6B left and right Zn(II) ions alone at concentration (0.3 ppm) showed little or no inhibition effect of MCF-7 breast cancer cells growth in aerobic under visible light irradiation conditions.

As shown in FIG. 6C left and right, TMPyP alone at experimental concentration (0.3 ppm) showed a nearly complete inhibition of growth of MCF-7 breast cancer cells under visible light irradiation. This confirms that reactive oxygen (singlet oxygen) produced from photosensitization reaction of TMPyP inhibits growth of breast cancer cells.

As depicted in FIG. 6D left and right, one variation of the claimed treatment composition, TMPyP+Zn(II) ions also inhibits growth of breast cancer under visible light irradiation. At the experimental concentration (0.3 ppm), the growth of MCF-7 breast cancer cells is significantly inhibited (from about 76% to 94%) at normal room temperature and pressure under visible light irradiation.

Furthermore, the treatment composition variation of associated TMPyP+Zn(II) ions has the potential to be used simultaneously or sequentially as antibacterial and chemotherapeutic agents under visible light irradiation.

Example 7

To determine the efficacy for singlet oxygen production in aqueous solution of claimed treatment composition, TMPyP+Zn(II) ions, $^1O_2$ quantum yield ($\phi_\Delta$) was calculated by using methylene blue as a standard with a known $\phi_\Delta$ of 0.52. DHN has been used as a singlet oxygen chemical probe to detect $^1O_2$ in aqueous solution. The reaction of DHN and singlet oxygen is reported to be very fast and produces Juglone as a principal product. $^1O_2$ quantum yield for treatment composition was calculated with Equation 1 by using $\phi_{\Delta(s)}$ of MB ($\phi_\Delta = 0.52$) reported in the prior art.

$$\Phi_{\Delta(x)} = \Phi_{\Delta(s)} \times \frac{S_x}{S_s} \times \frac{F_s}{F_x}$$ Equation 1

Above cited Equation 1 was followed to calculate $^1O_2$ quantum yield ($\phi_\Delta$) for treatment composition, TMPyP+Zn(II) in aqueous solution, where S is the slope of the plot of the absorbance versus irradiation, and F is the absorption correction factor. The singlet oxygen quantum yield ($\phi_\Delta$) of treatment composition, TMPyP+Zn(II) ions was calculated to be 0.57, which is similar to the $^1O_2$ quantum yield value for TMPyP. Therefore, the treatment composition possesses unique characteristics to be a good photosensitizer, which can be used to efficiently generate $^1O_2$ in aqueous solution for the treatment of bacterial infections as well as against cancers.

Figure 7:
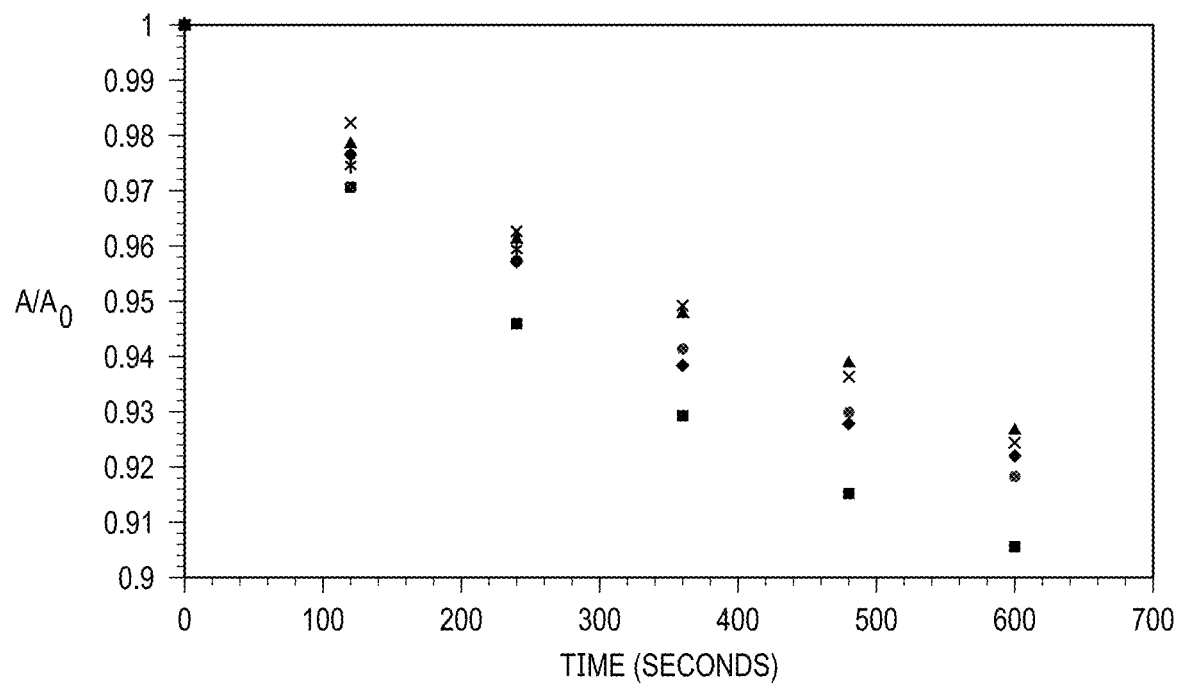
FIG. 7 is a plot of the rate of change of absorption monitored at 300 nm over 10 minutes as a function of irradiation time in aerobic conditions, conducted in the presence TMPyP without Zn (II) and at differing concentrations of Zn (II).

FIG. 7 shows the rate of change over 10 minutes time of DHN monitored at 300 nm as a function of visible light irradiation time in aerobic aqueous solution. Experiments were carried out in the presence of DHN ($1.2\times10^{-4}$ M) and TMPyP ($3.67\times10^{-7}$ M), and (i) and (i) Zinc (II) (0.075 ppm) (square); (ii) without Zinc (II) (triangle); (iii) Zinc (II) (0.15 ppm) (cross); Zinc (II) (0.3 ppm) (diamond); and Zinc (II) (1.2 ppm) (circle).

As depicted in FIG. 7, the results of the effect of Zn(II) ions on photooxidation of DHN revealed that the rate of photooxidation of DHN by TMPyP depends on the concentration of Zn(II) ions in aqueous solution. The photooxidation of DHN by TMPyP in the presence of Zn(II) ions (monitored at 300 nm) was observed to follow pseudo first order kinetics and the rate constants were determined by linear regression fitting of the experimental data (calculated absorbance values as $\ln(A_0)/(A)$ vs t, where $A_0$ is the absorbance at time 0, and A is the absorbance at time t).

Table 1 summarizes all rate constants of DHN photooxidation by TMPyP as a function of Zn(II) ions in aerobic aqueous solution under visible light irradiation.

TABLE 1

| Concentration of Zinc (II) (ppm) | Rate Constant, k ($s^{-1}$) | $R^2$ |
|---|---|---|
| 0.000 | $1.601 \times 10^{-4}$ | 0.9966 |
| 0.075 | $2.251 \times 10^{-4}$ | 0.9976 |
| 0.150 | $1.550 \times 10^{-4}$ | 0.9992 |
| 0.300 | $1.784 \times 10^{-4}$ | 0.9956 |
| 0.600 | $1.690 \times 10^{-4}$ | 0.9795 |
| 1.200 | $1.779 \times 10^{-4}$ | 0.9970 |

The rate constant of DHN photooxidation by TMPyP was calculated to be $1.601\times10^{-4}$ $s^{-1}$. Upon addition of 0.150 ppm Zn(II) ions, the rate of photooxidation of DHN by TMPyP increased (k=$1.550\times10^{-4}$ $s^{-1}$) compared to metal free solution. A rapid increase of photooxidation of DHN by TMPyP was seen upon addition of increasing amount of Zn(II) ions. Very surprisingly, upon addition of 0.075 ppm Zn(II) ions, the rate of photooxidation of DHN by TMPyP significantly increased (k=$2.251\times10^{-4}$ $s^{-1}$) indicating optimized reaction conditions of the photooxidation of DHN by TMPyP when Zn(II) concentration ranges from about 0.075 ppm to 1.200 ppm. A maximum rate of photooxidation of DHN by TMPyP was observed when Zn(II) ions concentration was about 0.075 ppm (k=$2.251\times10^{-4}$ $s^{-1}$).

It is a surprise, an unexpected discovery, that lower concentrations of metal ions increased significantly the rate of photooxidation. That is, I found I can vary ratio of metal ions to porphyrin and obtain unanticipated effects, including some random effects. I speculate, based on this data, that at lower concentration of metal ions (in range of 0.075 ppm), metal ions associate with TMPyP as a specific form of active complex with which can effectively produce singlet oxygen (1.45 times higher than concentrated zinc ions solution) and yet highest level is higher than intermediate ranges in above Table 1. At higher concentration of metal ions (0.150 ppm), the association, structure or form of porphyrin/metal complex is different than lower and intermediate likely more efficient than lower in quenching excited states of porphyrin leading to decrease in production of singlet oxygen. The inventive composition produced in situ singlet oxygen and active complex(s) in aqueous solution. A maximum rate of formation of these two products can be obtained by varying concentration of hMe(II) ions in the treatment composition.

Example 8

A series of control reactions were performed using above described materials, solutions, apparatus and methods in order to determine the nature of ROS produced by the claimed treatment composition, TMPyP+Zn(II) ions in solution.

Figure 8:
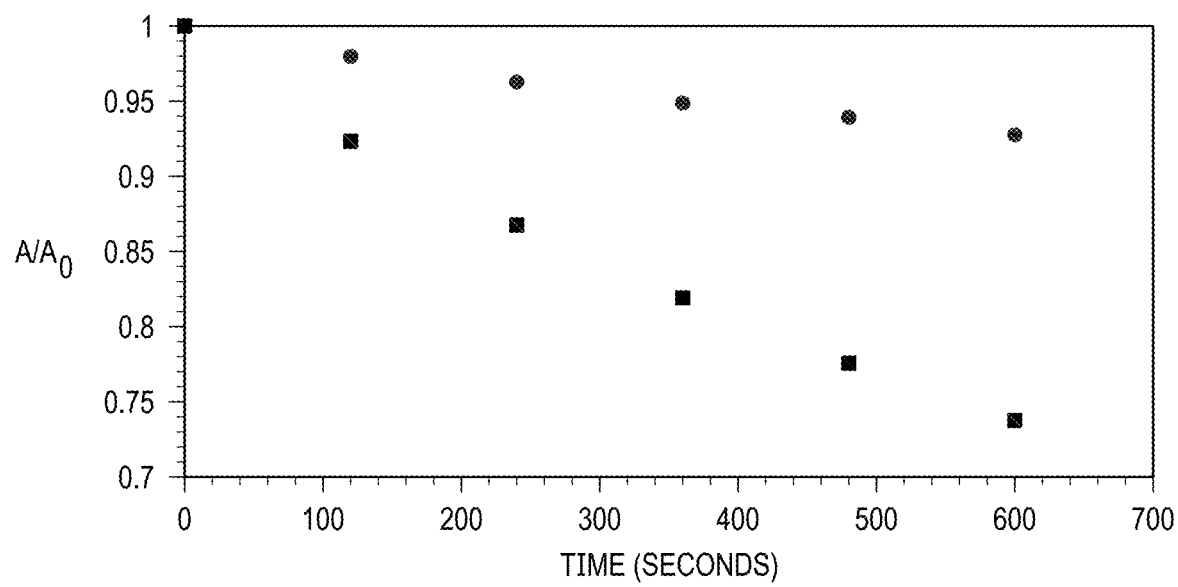
FIG. 8 is a plot of rate of change of absorption of DHN monitored at 300 nm as a function of irradiation time of various combinations and concentrations of DHN, TMPyP, $NaN_3$, zinc, $D_2O$, and $H_2O$.

FIG. 8 is a plot showing the rate of change over 20 minutes of DHN monitored at 300 nm as a function of irradiation time. Experiments were carried in the presence of DHN ($1.20\times10^{-4}$ M), TMPyP ($3.67\times10^{-7}$ M), and Zn (II) ($1.04\times10^{-6}$ M) in $H_2O$ (circles) against DHN ($1.20\times10^{-4}$ M), TMPyP ($3.67\times10^{-7}$ M), and Zn (II) ($1.04\times10^{-6}$ M) in $D_2O$ (triangles).

The rate of DHN photooxidation by TMPyP+Zn(II) ions was found to increase significantly in $D_2O$ medium compared to in $H_2O$ medium. This data strongly indicates that TMPyP+Zn(II) solution generates $^1O_2$ in aqueous solution, as shown in FIG. 8.

The O (oxygen) from hydrated metal cannot be the source of singlet oxygen unless water molecule in the hydrated metal is oxidized to oxygen, which then in turn changes into singlet oxygen. This is most unlikely to occur at the mild conditions used in experiments or those which are claimed.

Example 9

Figure 9:
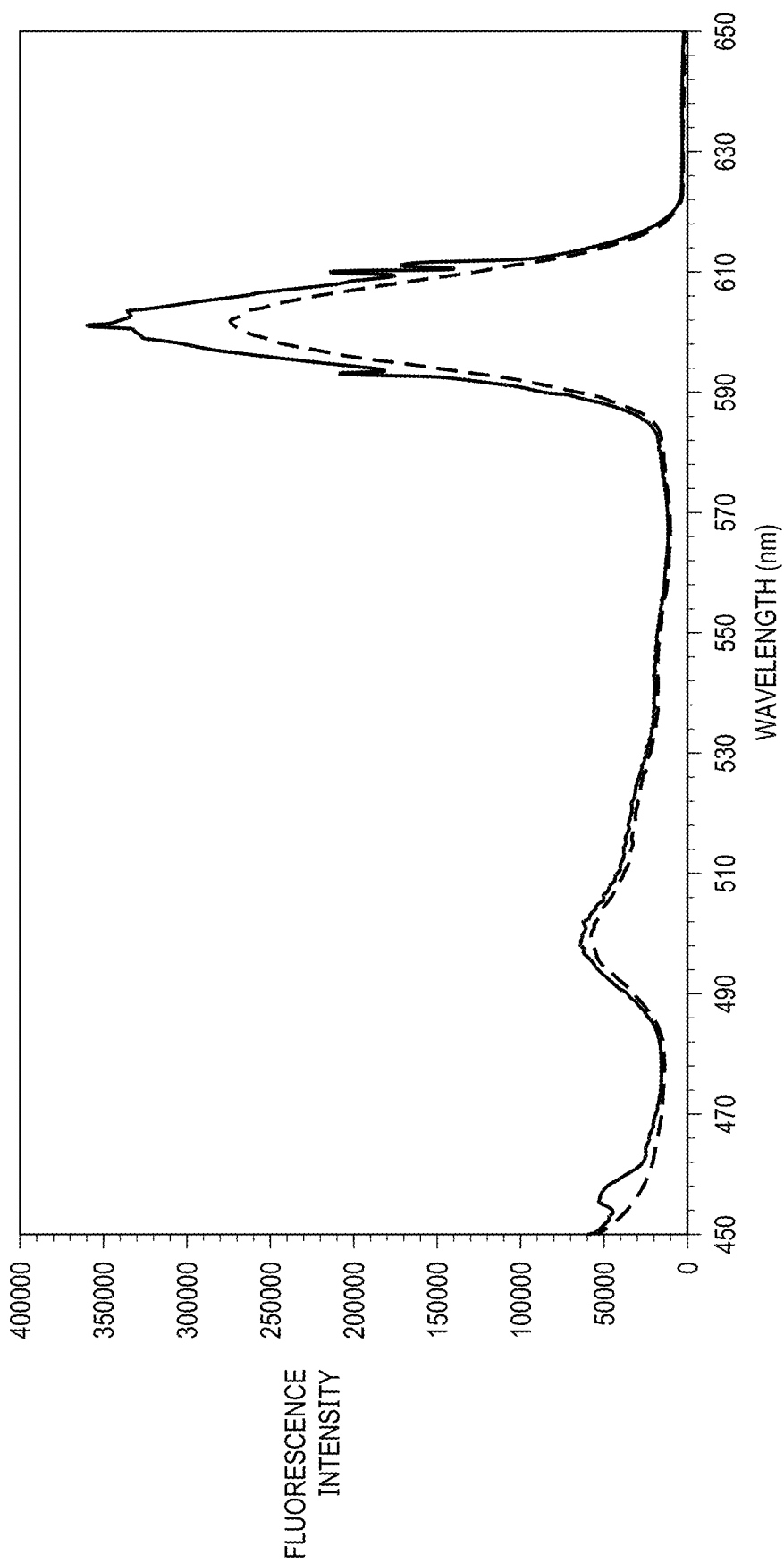
FIG. 9 is a plot of emissions for combination of TMPyP and Zn(II) in aqueous solution and shows the treatment composition is useful for image-guided PDT applications.
Figure 10B:
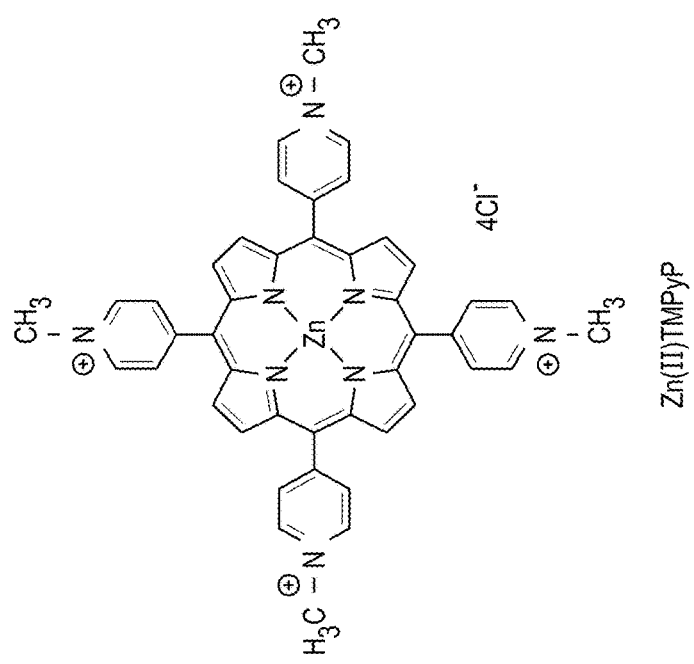
FIG. 10 is chemical structure drawing of commercially available TMPyP at FIG. 10A and at FIG. 10B commercially available conventional bound Zn(II)TMPyP where zinc is bound to porphyrin core.
Figure 11:
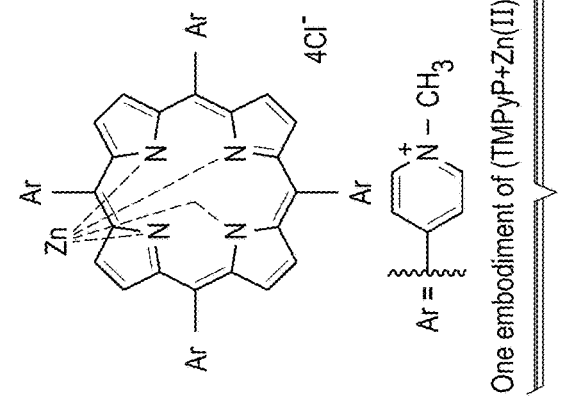
Figure 10A:
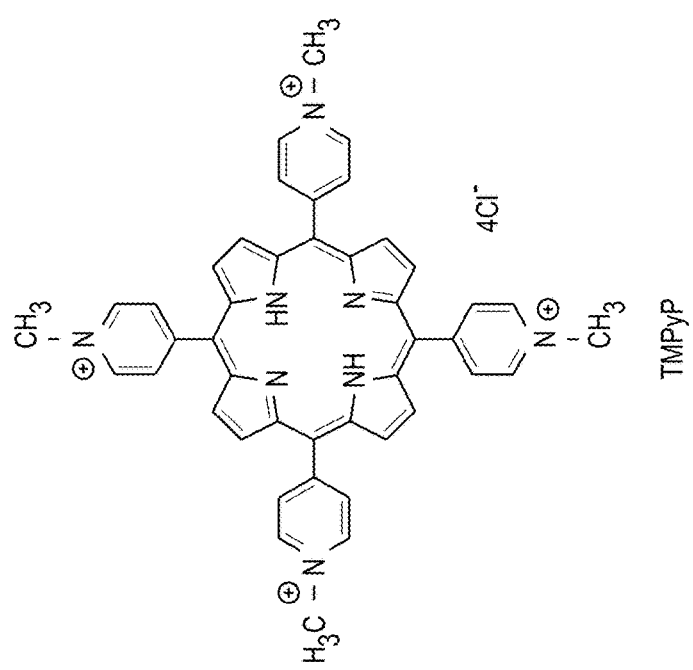

To determine the potential for image-guided photodynamic diagnostic application, fluorescence properties of an example of the claimed treatment solution were studied. FIG. 9 shows comparative emission spectra. Each experiment was run using the following instrumental parameters; Ex WL: 423 nm; Start: 433 nm; End: 800 nm; Ex Slit: 10.0 nm; Em Slit: 12.0 nm; Speed: 1000 nm/min; Gain: High; Auto Lamp: on.

FIG. 9 compares the fluorescence intensity of $1.0\times10^{-6}$ M TMPyP alone (dashed line) against $1.0\times10^{-6}$ M TMPyP with $1.0\times10^{-6}$ M Zn(II) ions, the treatment composition (solid line).

The study showed that, upon addition of Zn(II) ions to a TMPyP solution, an enhancement of fluorescence intensity of TMPyP was observed. Thus, claimed treatment composition (TMPyP+Zn(II)) is useful for image-guided PDT applications. The obtained experimental data teaches that treatment composition TMPyP+Zn(II) fluoresces in aqueous media and unexpectedly shows increased fluorescence intensity in the presence of Zn(II) ions at lower than expected concentrations.

As evidenced by above test results, the claimed zinc containing compositions are not toxic against eukaryotic cells (breast cancer cells) in dark conditions. As to excess Zn, Zn metal only exhibits toxic effects when it is used at higher doses in comparison to several other metal ions with similar chemical properties. According to Plum, M. L. et al (2010) "The essential toxin: impact of zinc on human health" *Int. J. Environ. Res. Public Health* 7, 1342-1365), "zinc is an essential trace element not only for humans, but for all organisms. Zinc is a component of more than 300 enzymes and an even greater number of other proteins, which emphasizes its indispensable role for human health. Optimal nucleic acid and protein metabolism, as well as cell growth, division, and function, require sufficient availability of zinc". According to above cited Plum, M. L. et al (and Toxnet database, U.S. National Library of Medicine) "the oral LD50 for zinc is close to 3 g/kg body weight, more than 10-fold higher than cadmium and 50-fold higher than mercury". U. S. National Library of Medicine, Toxnet Database available online via National Institute of Health. Thus claimed zinc-containing compositions could be substantially non-toxic under prescribed conditions.

Example 10

This Example evaluated iron(II), cobalt(II) and manganese(II), with and without presence of ArPP porphyrin, against control (porphyrin only without metal) and zinc (II) with and without ArPP porphyrin.

This Example confirms that hydrated divalent ions (hMe (II)), which have closely similar properties at the level of hydrated zinc ions form an effective treatment composition with free base tetrakis Ar substituted porphyrin core without bound metal or halide substitution at core (ArPP such as TMPyP). That is, this Example confirms that hMe(II) hydrated metals in +2 state which have comparable size or spatial geometry under combination or reaction conditions near that of Zn(II)+, where hMe(II) is to have a positive charge, and/or similar charge density, for illustration, akin to that of "Zn(II)+" are effective to form treatment compositions of this invention.

FIG. 12A control (TMPyP without combined metal) as expected shows in first row, first three boxes from left, no sign of inhibition of growth of bacteria when *E. coli* solution was treated with TMPyP alone (without bivalent metal present) in dark as well as in light conditions. FIG. 12A also shows no inhibition of growth of bacteria when TMPyP alone was applied to *E. coli* solution in dark conditions confirming non-toxicity of TMPyP alone against bacteria in dark. And likely since TMPyP is nontoxic to prokaryotic cells (bacteria), it should behave similarly as to eukaryotic cells (cancerous).

FIG. 12A control (first row, last box, far right) shows, as expected from prior art, show TMPyP exhibits 100% inhibition of growth of *E. coli* bacteria when TMPyP treats *E. coli* in light conditions. TMPyP produced in situ singlet oxygen which leads to cell death.

Iron is one of the trace metals within the human body.

FIG. 12B (second row, first two boxes from left) Iron(II) shows zero inhibition of growth of bacteria in dark as well as in light conditions when iron(II) was applied without TMPyP to *E. coli* bacteria.

FIG. 12B (second row, third box from left) shows however, quite surprisingly, divalent iron (II) association with TMPyP completely inhibits (100%) the growth of bacteria when iron (II) was combined at mild conditions with TMPyP and *E. coli* bacteria in dark conditions.

My earlier research as described in PCT/US2018/024338 (filed 26 Mar. 2018) shows a trivalent Fe (III) metal does not show any inhibition of growth of bacteria when combined at mild conditions with TMPyP and *E. coli* bacteria in dark conditions.

FIG. 12B (second row, fourth box from left) shows under light conditions, Fe(II) when combined with TMPyP, in solution of *E. coli* bacteria, causes 100% inhibition of growth of *E. coli* bacteria. Singlet oxygen and association complex, TMPyP+hFe(II) produced in situ from hydrated Fe(II) metal and TMPyP solution under light conditions leads to death of *E. coli* cells.

Manganese is another trace element within the human body.

FIG. 12C shows similar results obtained for divalent metal manganese (II).

FIG. 12C (third row, first two boxes from left) manganese (II) shows zero inhibition of growth of bacteria in dark as well as in light conditions when manganese (II) was applied without TMPyP to *E. coli* bacteria.

FIG. 12C (third row, third box from left) shows however, quite surprisingly, divalent manganese (II) association with TMPyP completely inhibits (100%) the growth of bacteria when manganese (II) was combined at mild conditions with TMPyP and *E. coli* bacteria in dark conditions.

FIG. 12C (third row, fourth box from left) shows under light conditions, manganese (II) when combined with TMPyP, in solution of *E. coli* bacteria, causes 100% inhibition of growth of *E. coli* bacteria. Singlet oxygen and association complex, TMPyP+hMn(II) produced in situ from hydrated Mn(II) metal and TMPyP solution under light conditions leads to death of *E. coli* cells.

FIG. 12D (fourth row) shows same results for zinc (II) metal confirming other Examples herein. This set of experiments further confirmed that the results are reproducible.

FIG. 12D (fourth row, first two box from left) shows no inhibition of growth of bacteria in dark as well as in light conditions was observed when zinc(II) alone is reacted with *E. coli* bacteria.

FIG. 12D (fourth row, last two boxes from left) show however, Zn (II) completely inhibits (100%) the growth of bacteria when it was reacted with TMPyP and *E. coli* bacteria in dark conditions. Under light conditions, Zn(II) shows 100% inhibition of growth of *E. coli* bacteria when it was reacted with TMPyP and solution of *E. coli* bacteria. Association complex of TMPyP+hZn(II) and singlet oxygen produced in situ from combination at mild conditions of Zn(II) metal and TMPyP solution under light conditions leads to death of *E. coli* cells.

Cobalt (II) is another trace metal within human body.

FIG. 12E shows similar results obtained for divalent metal cobalt (II).

FIG. 12E (fifth row, first two boxes from left) cobalt (II) shows zero inhibition of growth of bacteria in dark as well as in light conditions when cobalt (II) was applied without TMPyP to *E. coli* bacteria.

FIG. 12E (fifth row, third box from left) shows however, quite surprisingly, divalent cobalt (II) association with TMPyP completely inhibits (100%) the growth of bacteria when cobalt (II) was combined at mild conditions with TMPyP and *E. coli* bacteria in dark conditions.

FIG. 12E (fifth row, fourth box from left) shows under light conditions, cobalt (II) when combined with TMPyP, in solution of *E. coli* bacteria, causes 100% inhibition of growth of *E. coli* bacteria. Singlet oxygen and association complex, TMPyP+hCo(II) produced in situ from hydrated Co(II) metal and TMPyP solution under light conditions leads to death of *E. coli* cells.

Since claimed treatment compositions of associations of hMe(II)+ and ArPPh as shown in FIG. 12 produce antibacterial association complex(es) in situ and the formation of said complex does not dependent on oxygen gas, such compositions are thus an effective antibacterial in dark aerobic and dark anaerobic conditions as well as light aerobic and anaerobic conditions. Also, the claimed treatment compositions are capable of killing bacteria (effective against prokaryotic cells) in the presence of light. The claimed composition can kill bacteria via two mechanisms (a) active form of association complex, and (b) singlet oxygen generation in presence of light.

In addition, the claimed compositions are also capable of killing cancers (effective against eukaryotic cells), in the presence of light and with other activation agent; that is, the claimed compositions are capable of killing cancers via singlet oxygen mechanism.

As known in the art, the treatment compositions of this invention may also contain minor amounts of nontoxic, auxiliary substances such as diluents and buffering agents and others. Fluorescence diagnostics are performed by visual or by fiber optic probes well known in the art.

Also as known in the art for the treatment of superficial tumors or skin disorders, the compositions may be topically administered using standard topical compositions involving typical excipients in the form of liquids, creams, gels, ointments, aerosols or others known in the art. In addition to in vivo use, compositions of this invention can be used in vitro to treat bacterial infectious agents. For illustration, not limitation, blood plasma or blood for transfusion can be treated with the compositions of this invention, and when desired, irradiated with appropriate light source as taught herein.

Again, it is important that I have discovered treatment compositions that can easily be prepared from commercially available chemicals, and without special equipment, skills or training required, allowing potential for them to be readily available at lower cost in developing and developed countries. As demonstrated by the Examples, short preparation and application times for compositions of this invention enables rapid, effective field treatments, and may include certain diagnosis, in locations at which any kind of treatments or diagnosis were heretofore prohibited.

Thus in various embodiments variations of claimed compositions and methods are one or more chemotherapeutic therapies. Claimed compositions and methods can be effective for either treatment or diagnosis of malignancy, bacterial infections This invention can be applied to bacteria that include, but are not limited to, bacterial skin infections (including but not limitation necrotizing fasciitis), food born bacterial infections, sexually transmitted bacterial infections, bacterial meningitis, otitis media, urinary tract infections, respiratory tract infections or bacteria associated with malignant or other tumors. This invention can also be applied to treat other tissues and pathologies or issues such as Alzheimer's symptoms While the above described and claimed inventions have been described with reference to specific embodiments of treatment compositions and methods of making and using to impair or terminate bacterial infections and/or cancers, it should thus be understood that the foregoing disclosure is illustrative and not limiting, and that obvious modifications may be made by those skilled in the art without departing from the spirit of this invention.

The invention claimed is:

1. A treatment or diagnosis composition comprising:
 a complex comprising:
 TMPyP (meso-tetra(N-methyl-4-pyridyl) porphyrin tetrachloride) without bound core metal or halide substitution at core, and
 a hydrated metal, wherein the hydrated metal has an +2 oxidation state (hMe(II)),
 wherein a mole ratio of TMPyP to hMe(II) is from 1:2 to 1:3.

2. The composition of claim 1, wherein
 the hMe(II) includes one or more of Zn(II), Co(II), Fe(II), and Mn(II).

3. The composition of claim 1, wherein the hMe(II) includes hZn(II).

4. The composition of claim 1, wherein hMe(II) is hZn (II).

5. The composition of claim 1, further comprising a reactive oxygen species.

6. The composition of claim 2, wherein the reactive oxygen species is singlet oxygen ($^1O_2$), an antibacterial agent, or combinations thereof.

7. A method of treating cancer comprising:
providing a complex comprising,
TMPyP (meso-tetra(N-methyl-4-pyridyl) porphyrin tetrachloride) without bound core metal or halide substitution at core, and
a hydrated metal, wherein the hydrated metal has an +2 oxidation state (hMe(II)),
wherein a mole ratio of TMPyP to hMe(II) is from 1:2 to 1:3,
wherein the hMe(II) includes one or more of Zn(II), Co(II), Fe(II), and Mn(II), and
treating the cancer by administering the complex by injection.

8. The method of claim 7, wherein the hMe(II) includes hZn(II).

9. The method of claim 7, further comprising providing visible light irradiation.

10. A method of treating a bacterial infection comprising:
providing a complex comprising,
TMPyP (meso-tetra(N-methyl-4-pyridyl) porphyrin tetrachloride) without bound core metal or halide substitution at core, and
a hydrated metal, wherein the hydrated metal has an +2 oxidation state (hMe(II)),
wherein a ratio of TMPyP to hMe(II) is from 1:2 to 1:3, and
wherein the hMe(II) includes one or more of Zn(II), Co(II), Fe(II), and Mn(II), and
inhibiting a bacterial growth or killing a bacteria of the bacterial infection by administering the complex by injection.

11. The method of claim 10, wherein the bacterial infection includes necrotizing fasciitis, food born bacterial infections, sexually transmitted bacterial infections, bacterial meningitis, otitis media, urinary tract infections, respiratory tract infections, or bacteria associated with malignant or other tumors.

12. The method of claim 11, wherein the bacterial infection includes *E. coli* bacteria.

13. The method of claim 10, further comprising:
providing visible light irradiation.

14. The method of claim 10, further comprising:
providing dark conditions.

15. The composition of claim 1, wherein the ratio of mole ratio of TMPyP to hMe(II) is an average of 1:2.85.

* * * * *